US011225677B2

(12) United States Patent
Liu et al.

(10) Patent No.: US 11,225,677 B2
(45) Date of Patent: Jan. 18, 2022

(54) LONG-CHAIN DIBASIC ACID WITH LOW CONTENT OF MONOBASIC ACID IMPURITY AND THE PRODUCTION METHOD THEREOF

(71) Applicants: Cathay Biotech Inc., Shanghai (CN); CIBT America Inc., Newark, DE (US)

(72) Inventors: Wenbo Liu, Shanghai (CN); Min Xu, Shanghai (CN); Chen Yang, Shanghai (CN); Howard Chou, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/503,301

(22) Filed: Jul. 3, 2019

(65) Prior Publication Data

US 2020/0010863 A1 Jan. 9, 2020

(30) Foreign Application Priority Data

Jul. 6, 2018 (CN) ......................... 201810734190.8
Jul. 6, 2018 (CN) ......................... 201810734273.7
Apr. 22, 2019 (CN) ......................... 201910321614.2

(51) Int. Cl.
*C12P 7/64* (2006.01)
*C12N 9/02* (2006.01)

(52) U.S. Cl.
CPC .......... *C12P 7/6409* (2013.01); *C12N 9/0071* (2013.01)

(58) Field of Classification Search
CPC ..... C12P 7/6409; C12N 9/0071; C12N 15/01; C12Y 114/14
See application file for complete search history.

(56) References Cited

FOREIGN PATENT DOCUMENTS

| | | | |
|---|---|---|---|
| EP | 3550014 | A1 | 10/2019 |
| WO | WO 2013/006730 | | 1/2013 |

OTHER PUBLICATIONS

Pedrini et al. Molecular characterization and expression analysis of a suite of cytochrome P450 enzymes implicated in insect hydrocarbon degradation in the entomopathogenic fungus *Beauveria bassiana*. Microbiol (2010), 156, 2549-2557.*
Craft et al., "Identification and Characterization of the CYP52 Family of Candida tropicalis ATCC 20336, Important for the Conversion of Fatty Acids and Alkanes to α,ω-Dicarboxylic Acids", Appl. Environ. Microbiol. 2003, 69(10):5983-5991.
Extended European Search report for Application No. 19184887.8, dated Nov. 15, 2019, 13 pages.
Werner et al., "Biotechnological production of bio-based long-chain dicarboxylic acids with oleogenious yeasts", World J Microbiol Biotechnol (2017) 33:194.

* cited by examiner

*Primary Examiner* — Iqbal H Chowdhury
(74) *Attorney, Agent, or Firm* — Adsero IP

(57) ABSTRACT

The invention relates to a long-chain dibasic acid with low content of monobasic acid impurity and a production method thereof, in particular to the preparation of a long-chain dibasic acid producing strain by means of directed evolution and homologous recombination, and to the production of a long-chain dibasic acid with low content of monobasic acid impurity by fermentation of said strain. The invention relates to a mutated CYP52A12 gene, homologous gene or variant thereof, which, relative to GenBank Accession Number AY230498 and taking the first base upstream of the start codon ATG as −1, comprises a mutation. The invention relates to a strain comprising said mutated CYP52A12 gene, homologous gene or variant thereof wherein when the strain is fermented to produce a long-chain dibasic acid, the content of monobasic acid impurity in the fermentation product is significantly reduced.

9 Claims, 2 Drawing Sheets

Specification includes a Sequence Listing.

```
192  GTCGACTTCTCCTTTAGGCAATAGAAAAAGACTAAGAGAACAGCGTTTTTACAGGTTGCA
430  GTCGACTTCTCCTTTAGGCAATAGAAAAAGACTAAGGGAACAGCGTTTTTACAGGTTGCT
     *********************************** ******************** *
192  TTGGTTAATGTAGTATTTTTTTAGTCCCAGCATTCTGTGGGTTGCTCTGGGTTTCTAGAA
430  TTGGTTAATGTAGTATTTTTT-AGTCCAA-CATTCTGTGGGTTGCTCTGGGTTTCTAGAA
     ********************* ***** * ******************************
192  TAGGAAATCACAGGAGAATGCAAATTCAGATGGAAGAACAAAGAGATAAAAAACAAAAAA
430  TAGGAAATCACAGGAGAATGCAAATTCAGATGGAAGAACAAAGAGATAAAAAACAAAAAA
     ************************************************************
192  AAACTGAGTTTTGCACCAATAGAATGTTTGATGATATCATCCACTCGCTAAACGAATCAT
430  AAACTGAGTTTTGCACCAATAGAATGTTTGATGATATCATCCACTCGCTAAACGAATCAT
     ************************************************************
192  GTGGGTGATCTTCTCTTTAGTTTTGGTCTATCATAAAACACATGAAAGTGAAATCCAAAT
430  GTGGGTGATCTTCTCTTTAGTTTTGGTCTATCATAAAACACATGAAAGTGAAATCCAAAT
     ************************************************************
192  ACACTACACTCCGGGTATTGTCCTTCGTTTTACAGATGTCTCATTGTCTTACTTTTGAGG
430  ACACTACACTCCGGGTATTGTCCTTCGTTTTACGGATGTCTCATTGTCTTACTTTTGAGG
     ********************************* **************************
192  TCATAGGAGTTGCCTGTGAGAGATCACAGAGATTATCACACTCACATTTATCGTAGTTTC
430  TCATAGGAGTTGCCTGTGAGAGATCACAGAGATTATCACACTCACATTTATCGTAGTTTC
     ************************************************************
192  CTATCTCATGCTGTGTGTCTCTGGTTGGTTCATGAGTTTGGATTGTTGTACATTAAAGGA
430  CTATCTCATGCTGTGTGTCTCTGGTTGGTTCATGAGTTTGGATTGTTGTACATTAAAGGA
     ************************************************************
192  ATCGCTGGAAAGCAAAGCTAACTAAATT--TTCTTTGTCACAGGTACACTAACCTGTAAA
430  ATCGCTGGAAAGCAAAGCTATTTAAATTTTTTCTTTGTCACAGGTACACTAACCTGTAAA
     ******************** ******   ******************************
192  ACTTCACTGCCACGCCAGTCTTTCCTGATTGGGCAAGTGCACAAACTACAACCTGCAAAA
430  ACTTCACTGCCACGCCAGTCTTTCCTGATTGGGCAAGTGCACAAACTACAACCTGCAAAA
     ************************************************************
192  CAGCACTCCGCTTGTCACAGGTTGTCTCCTCTCAACCAACAAAAAAATAAGATTAAACTT
430  CAGCACTCCGCTTGTCACAGGTTGTCTCCTCTCAACCAACAAAAAAATAAGATTAAACTT
     ************************************************************
192  TCTTTGCTCATGCATCAATCGGAGTTATCTCTGAAAGAGTTGCCTTTGTGTAATGTGTGC
430  TCTTTGCTCATGCATCAATCGGAGTTATCTCTGAAAGAGTTGCCTTTGTGTAATGTGTGC
     ************************************************************
192  CAAACTCAAACTGCAAAACTAACCACAGAATGATTTCCCTCACAATTATATAAACTCACC
430  CAAACTCAAACTGCAAAACTAACCACAGAATGATTTCCCTCACAATTATATAAACTCACC
     ************************************************************
192  CACATTTCCACAGACCGTAATTTCATGTCTCACTTTCTCTTTTGCTCTTCTTTTACTTAG
430  CACATTTCCACAGACCGTAATTTCATGTCTCACTTTCTCTTTTGCTCTTCTTTTACTTAG
     ************************************************************
192  TCAGGTTTGATAACTTCCTTTTTTATTACCCTATCTTATTTATTTATTTATTCATTTATA
430  TCAGGTTTGATAACTTCCTTTTTTATTACCCTATCTTATTTATTTATTTATTCATTTATA
     ************************************************************
192  CCAACCAACCAACC
430  CCAACCAACC----
     **********
```

Figure 2

LONG-CHAIN DIBASIC ACID WITH LOW CONTENT OF MONOBASIC ACID IMPURITY AND THE PRODUCTION METHOD THEREOF

CROSS-REFERENCE TO RELATED APPLICATIONS

This application claims priority to and the benefit of Chinese Patent Application No. 201810734273.7, filed on Jul. 6, 2018 and Chinese Patent Application No. 201810734190.8 filed on Jul. 6, 2018, and Chinese Patent Application No. 201910321614.2, filed on Apr. 22, 2019, the disclosures of which are incorporated herein by reference in their entirety.

SEQUENCE STATEMENT

Incorporated by reference herein in its entirety is the Sequence Listing entitled "0503.13_ST25.txt", size of 76 kilobytes, created Feb. 3, 2021.

FIELD OF THE INVENTION

The invention relates to a long-chain dibasic acid with low content of monobasic acid impurity and a preparation method thereof; as well as to a method for preparing a long-chain dibasic acid producing strain by using directed evolution and homologous recombination, and a method for producing a long-chain dibasic acid with low content of monobasic acid impurity by using said strain.

BACKGROUND

Long-chain dibasic acid (LCDA; also referred to as long chain dicarboxylic acid or long chain diacid) is a dibasic acid comprising the formula $HOOC(CH_2)_nCOOH$, where $n \geq 7$. As important monomer raw materials, long-chain dibasic acids are widely used in the synthesis of nylon, resins, hot-melt adhesives, powder coatings, preservatives, perfumes, lubricants, plasticizers, and the like.

For a long time, long-chain dibasic acids are synthesized via classical chemical synthesis pathway from the petroleum, such as butadiene multiple-step oxidation process. The Chemical synthesis methods face many challenges. Dibasic acid obtained by the chemical synthesis method is a mixture of long-chain dibasic acid and short-chain dibasic acid, and thus the subsequent complicated extraction and purification steps are necessary, which become a huge obstacle for production technique and production cost. Microbiological fermentation technology of producing a long-chain dibasic acid is advantageous over classical chemical synthesis method because it produces less pollution, is environment friendly, and is capable of synthesizing a long-chain dibasic acid such as the one having more than 12 carbon atoms which is difficult to be produced by chemical synthesis methods and has high purity and the like.

But using the microbiological fermentation method for producing a long-chain dibasic acid, there are residual impurities in the product sometimes and the reduction in the product purity affects the quality of the product significantly, which greatly affects its later application. In particular, the impurity which is characteristically similar to long-chain dibasic acid not only generates technical challenges to the later extraction and purification, but also produces great negative effects on the production cost control. Therefore, to genetically modify a strain for producing a long-chain dibasic acid so as to reduce the content of certain impurity during fermentation is important and valuable in industry to dibasic acid production via biological synthesis.

Previously, the improvement of a dibasic acid producing strain was mostly achieved through conventional random mutagenesis or genetic engineering methods. Due to the characteristic of random mutagenesis, there is a high requirement for screening throughput, and a new round of mutagenesis screening is required for each changed trait, which has become an important limiting factor technically. The genetic engineering means can be used to perform targeted genetic modification of a strain, so as to obtain a good strain with higher yield. The microbiological fermentation method of a long-chain dibasic acid is mainly based on ω-oxidation of alkane, which can then be degraded by β-oxidation pathway. Previous studies have shown that the yield of a long-chain dibasic acid can be increased by means of enhancing the ω-oxidation pathway and inhibiting the β-oxidation pathway. Pictaggio et al. of Coginis company (Mol. Cell. Biol., 11(9), 4333-4339, 1991) reported that knocking out two alleles of each of POX4 and POX5 could effectively block the β-oxidation pathway to achieve 100% conversion rate of the substrate. Further overexpression of the genes of two key enzymes, P450 and oxidoreductase CPR-b, of the rate-limiting step in the ω-oxidation pathway could effectively increase production. Xiaoqin Lai et al. (Chinese patent CN103992959B) reported that the introduction of one copy of the CYP52A14 gene into a dibasic acid producing strain could also effectively increase the conversion rate and production efficiency of the dibasic acid. In addition, Zhu'an Cao et al. (Biotechnol. J., 1, 68-74, 2006) from Tsinghua University found that knocking out a copy of the key gene CAT in the transportation of acetyl coenzyme A from peroxisome to mitochondria could partially block acetyl coenzyme A entering the citric acid cycle, and also effectively reduce the degradation of dibasic acids.

Error-prone PCR is the technique proposed by Leung et al. (Technical, 1, 11-15, 1989) to construct a gene library for directed studies. By changing PCR conditions, such as adjusting the concentration of four deoxyribonucleic acids in the reaction system, changing the concentration of $Mg^{2+}$, and using a low-fidelity DNA polymerase and the like, the bases are mismatched so as to introduce a mutation. Too high or too low mutation rate will affect the effect of constructing mutant libraries. The ideal base mutation ratio is 1-3 per DNA fragment. Therefore, the beneficial mutations that contribute to further improvement of the strain productivity can be screened through gene-directed genetic modification by using error-prone PCR of generating random mutations in combination with homologous recombination.

Previous studies on dibasic acid producing strains focused on random mutagenesis or overexpression of a gene in the upstream synthetic pathway or blocking the downstream β-oxidation pathway, and the directed evolution of a gene in the metabolic pathway has not been reported or applied. There is still a need in the art for a strain that significantly increases the yield of a long-chain dibasic acid and significantly reduces the content of some impurities, as well as preparation methods thereof.

SUMMARY OF THE INVENTION

The invention relates to an isolated mutated CYP52A12 gene, homologous gene or variant thereof, which, relative to GenBank Accession Number AY230498 (e.g. set forth in SEQ ID NO: 21, in particular nucleotides 1-1176 or 265-

1176) and taking the first base (e.g. the base "C" at position 1176 of SEQ ID NO: 21) upstream of the start codon ATG (wherein "A" is position 1) as −1, comprises any one or more of the following base mutations: −876A>G; −853A>T; −831delT; −825C>A; −823delG; −579A>G; −412_−411AC>TT; −402insTT and −15_1 ACCAACCAACCAACCA (SEQ ID NO.:37)>ACCAACCAACCA (SEQ ID NO.: 38) (e.g. −7_−4delACCA), wherein the variant has at least 70% sequence identity to the mutated CYP52A12 gene or homologous gene thereof.

In an embodiment, the mutated CYP52A12 gene, homologous gene or variant thereof comprises the base mutation −15_1 ACCAACCAACCAACCA (SEQ ID NO.: 37)>ACCAACCAACCA (SEQ ID NO.: 38) (e.g. −7_−4delACCA), e.g. set forth in SEQ ID NO: 22.

In an embodiment, the mutated CYP52A12 gene, homologous gene or variant thereof comprises the base mutations −412_−411AC>TT; −402insTT and −15_1 ACCAACCAACCAACCA (SEQ ID NO.:37)>ACCAACCAACCA (SEQ ID NO.: 38) (e.g. −7_−4delACCA), e.g. set forth in SEQ ID NO: 23.

In an embodiment, the mutated CYP52A12 gene, homologous gene or variant thereof comprises the base mutations −579A>G; −412_−411AC>TT; −402insTT and −15_1 ACCAACCAACCAACCA (SEQ ID NO.:37)>ACCAACCAACCA (SEQ ID NO.: 38) (e.g. −7_−4delACCA), e.g. set forth in SEQ ID NO: 24.

In an embodiment, the mutated CYP52A12 gene, homologous gene or variant thereof comprises the base mutations −831delT; −825C>A; −823delG; −579A>G; −412_−411AC>TT; −402insTT and −15_1 ACCAACCAACCAACCA (SEQ ID NO.:37)>ACCAACCAACCA (SEQ ID NO.: 38) (e.g. −7_−4delACCA), e.g. set forth in SEQ ID NO: 25.

In an embodiment, the mutated CYP52A12 gene, homologous gene or variant thereof comprises the base mutations −876A>G; −853A>T; −831delT; −825C>A; −823delG; −579A>G; −412_−411AC>TT; −402insTT and −15_1 ACCAACCAACCAACCA (SEQ ID NO.:37)>ACCAACCAACCA (SEQ ID NO.: 38) (e.g. −7_−4delACCA), e.g. set forth in SEQ ID NO: 26.

The invention relates to an isolated DNA molecule, which, relative to nucleotides 1-1176 or 265-1176 of SEQ ID NO: 21, comprises any one or more of the following base mutations 301A>G, 324A>T, 346delT, 352C>A, 354delG, 598A>G, 765_766AC>TT, 774insTT and 1162_1176ACCAACCAACCAACC (SEQ ID NO.: 39)>ACCAACCAACC (SEQ ID NO.:40)(e.g. 1170_1173delACCA).

In an embodiment, the isolated DNA molecule comprises the base mutation 1162_1176ACCAACCAACCAACC (SEQ ID NO.: 39)>ACCAACCAACC (SEQ ID NO.:40) (e.g. 1170_1173delACCA), e.g. set forth in SEQ ID NO: 27 or 32.

In an embodiment, the isolated DNA molecule comprises the base mutations 765_766AC>TT, 774insTT and 1162_1176ACCAACCAACCAACC (SEQ ID NO.: 39)>ACCAACCAACC (SEQ ID NO.:40) (e.g. 1170_1173delACCA), e.g. set forth in SEQ ID NO: 28 or 33.

In an embodiment, the isolated DNA molecule comprises the base mutations 598A>G, 765_766AC>TT, 774insTT and 1162_1176ACCAACCAACCAACC (SEQ ID NO.: 39)>ACCAACCAACC (SEQ ID NO.:40) (e.g. 1170_1173delACCA), e.g. set forth in SEQ ID NO: 29 or 34.

In an embodiment, the isolated DNA molecule comprises the base mutations 346delT, 352C>A, 354delG, 598A>G, 765_766AC>TT, 774insTT and 1162_1176ACCAACCAACCAACC (SEQ ID NO.: 39)>ACCAACCAACC (SEQ ID NO.:40) (e.g. 1170_1173delACCA), e.g. set forth in SEQ ID NO: 30 or 35.

In an embodiment, the isolated DNA molecule comprises the base mutations 301A>G, 324A>T, 346delT, 352C>A, 354delG, 598A>G, 765_766AC>TT, 774insTT and 1162_1176ACCAACCAACCAACC(SEQ ID NO.: 39)>ACCAACCAACC (SEQ ID NO.:40) (e.g. 1170_1173delACCA), e.g. set forth in SEQ ID NO: 31 or 36.

In an embodiment, the sequence of the mutated CYP52A12 gene according to the invention is set forth in any of SEQ ID NOs. 16 and 22-26 or a sequence having at least 70% sequence identity thereto, for example at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, or 99.96% sequence identity.

The invention further relates to a microorganism containing the isolated DNA molecule (for controlling the expression of CYP52A12 gene, e.g. as a promoter) or the mutated CYP52A12 gene, homologous gene or variant thereof according to the invention, which produces a long-chain dibasic acid with a reduced content of monobasic acid impurity, compared to a microorganism containing a non-mutated CYP52A12 gene or homologous gene thereof.

The invention further relates to a method of producing a long-chain dibasic acid by fermentation with a microorganism containing the isolated DNA molecule or the mutated CYP52A12 gene, homologous gene or variant thereof according to the invention, comprising a step of culturing the microorganism, and optionally a step of isolating, extracting and/or purifying the long-chain dibasic acid from the culture.

In some embodiments, after the completion of the process of producing a long-chain dibasic acid by fermentation with a microorganism according to the invention, the mass ratio of monobasic acid impurity in fermentation broth is below 5%, wherein the mass ratio is the mass percentage of the monobasic acid impurity to the long-chain dibasic acid in the fermentation broth.

In some embodiments, after the completion of the process of producing a long-chain dibasic acid by fermentation with a microorganism according to the invention, the content of monobasic acid impurity in the fermentation broth, compared with that of the monobasic acid impurity in the long-chain dibasic acid produced by fermentation method with a conventional microorganism, such as by fermentation with a non-mutant microorganism according to the invention, is decreased by at least 5%.

The invention also relates to a long-chain dibasic acid with low content of monobasic acid impurity, wherein the content of monobasic acid impurity is greater than 0, and less than 12,000 ppm, preferably less than 10,000 ppm or 6,000 ppm, more preferably less than 3,000 ppm, more preferably less than 1,000 ppm, more preferably less than 500 ppm, more preferably less than 200 ppm; and wherein the monobasic acid impurity comprises a long-chain monocarboxylic acid impurity, i.e. containing only one carboxyl group (—COOH) in the carboxylic acid molecule.

In some embodiments, the long-chain dibasic acid producing microorganism strain according to the invention contains the isolated DNA molecule (for controlling the expression of CYP52A12 gene, e.g. as a promoter) or the mutated CYP52A12 gene, homologous gene or variant thereof according to the invention. In some embodiments, the long-chain dibasic acid producing microorganism strain is the microorganism according to the invention which contains the isolated DNA molecule or the mutated CYP52A12 gene, homologous gene or variant thereof according to the invention.

In some embodiments, the microorganism of the invention is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*. In a particular embodiment, the microorganism is CCTCC M2011192 or CCTCC M203052.

In some embodiments, the long-chain dibasic acid is selected from C9 to C22 long-chain dibasic acids, preferably selected from C9 to C18 long-chain dibasic acids, more preferably one or more of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one or more selected from the group consisting of sebacic acid, undecanedioic acid, dodecanedioic acid, tridecanedioic acid, tetradecanedioic acid, pentadecanedioic acid and hexadecanedioic acid.

In some embodiments, the monobasic acid impurity according to the invention has the formula of $CH_3$—$(CH_2)$n-COOH, where n≥7, and/or $CH_2OH$—$(CH_2)$n-COOH, where n≥7;

preferably the monobasic acid impurity comprises, but not limited to, a long-chain monobasic acid with the number of carbon atoms in the carbon chain being greater than 9; preferably the monobasic acid impurity comprises any one or more of a monobasic acid having 9 carbon atoms, a monobasic acid having 10 carbon atoms, a monobasic acid having 11 carbon atoms, a monobasic acid having 12 carbon atoms, a monobasic acid having 13 carbon atoms, a monobasic acid having 14 carbon atoms, a monobasic acid having 15 carbon atoms, a monobasic acid having 16 carbon atoms, a monobasic acid having 17 carbon atoms, a monobasic acid having 18 carbon atoms, and a monobasic acid having 19 carbon atoms.

In some embodiments, where the long-chain dibasic acid is C12 dibasic acid e.g. dodecanedioic acid, the monobasic acid impurity is predominantly a monobasic acid impurity having 12 carbon atoms, and the content of the monobasic acid impurity having 12 carbon atoms is less than 8,000 ppm.

In some embodiments, where the long-chain dibasic acid is C10 dibasic acid e.g. decanedioic acid, the monobasic acid impurity is predominantly a monobasic acid impurity having 10 carbon atoms, and the content of the monobasic acid impurity having 10 carbon atoms is less than 2,500 ppm.

In some embodiments, where the long-chain dibasic acid is C16 dibasic acid e.g. hexadecanedioic acid, the monobasic acid impurity is predominantly a monobasic acid impurity having 16 carbon atoms, and the content of the monobasic acid impurity having 16 carbon atoms is less than 12,000 ppm.

The invention further relates to a method of modifying a long-chain dibasic acid producing microorganism strain, comprising a step of directed evolution of a key gene in the pathway of the long-chain dibasic acid synthesis, wherein, compared to the microorganism strain before modified, the modified long chain dibasic acid producing microorganism strain is capable of producing the long chain dibasic acid with substantially decreased content of monobasic acid impurity, e.g. under the same conditions. In some embodiments, the key gene in the pathway of the long-chain dibasic acid synthesis is CYP52A12 gene.

In some embodiments, the microorganism of the invention is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*. In a particular embodiment, the microorganism is CCTCC M2011192 or CCTCC M203052.

In some embodiments, the long-chain dibasic acid according to the invention is selected from C9 to C22 long-chain dibasic acids, preferably selected from C9 to C18 long-chain dibasic acids, more preferably one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one or more selected from the group consisting of sebacic acid, undecanedioic acid, dodecanedioic acid, tridecanedioic acid, tetradecanedioic acid, pentadecanedioic acid and hexadecanedioic acid.

In some embodiments, the content of monobasic acid impurity, compared with that of the monobasic acid impurity in the long-chain dibasic acid produced by fermentation method with a conventional microorganism, is decreased by at least 5%, preferably at least 10%, more preferably at least 20%, more preferably at least 40%, and more preferably at least 50% or more.

In some embodiments, the method of modifying a long-chain dibasic acid producing microorganism strain comprises steps of:

1) preparing a target gene (CYP52A12 gene) fragment having a mutation by error-prone PCR;

2) preparing fragments upstream and downstream of the target gene (CYP52A12 gene) necessary for homologous recombination as templates for homologous recombination with a resistance marker gene, preferably the resistance marker gene is hygromycin B;

3) preparing a complete recombination fragment by PCR overlap extension;

4) introducing the recombination fragment into a strain by homologous recombination;

5) screening positive strains by means of the resistance marker;

6) screening strains wherein the content of monobasic acid impurity in the fermentation broth after completion of fermentation is significantly decreased;

7) optionally, removing the resistance marker in the screened strains by further homologous recombination.

The invention further relates to a fermentation broth during a process of producing a long-chain dibasic acid by fermentation with a microorganism, wherein the fermentation broth contains monobasic acid impurity, and the mass ratio of monobasic acid impurity is less than 5%, preferably less than 1.5%, more preferably less than 1.0%, less than 0.9%, wherein the mass ratio is the mass percentage of monobasic acid impurity to the long-chain dibasic acid in the fermentation broth.

Preferably, the long-chain dibasic acid is selected from C9 to C22 long-chain dibasic acids, and the monobasic acid impurity comprises, but not limited to, a long-chain monobasic acid with the number of carbon atoms in the carbon chain being greater than 9.

In some embodiments, the microorganism contains the isolated DNA molecule (for controlling the expression of CYP52A12 gene, e.g. as a promoter) or the mutated CYP52A12 gene, homologous gene or variant thereof according to the invention. In some embodiments, the microorganism is the microorganism according to the invention which contains the isolated DNA molecule or the mutated CYP52A12 gene, homologous gene or variant thereof according to the invention. In some embodiments, the fermentation broth is obtained by a method of producing a long-chain dibasic acid by fermentation with a microorganism containing the isolated DNA molecule or the mutated CYP52A12 gene, homologous gene or variant thereof according to the invention. In some embodiments, the fermentation broth is obtained in a process of producing a long-chain dibasic acid with a microorganism obtained by the method of modifying a long-chain dibasic acid producing microorganism strain according to the invention.

The invention further relates to a method of producing a long-chain dibasic acid as described in the invention, comprising obtaining a long-chain dibasic acid producing microorganism strain containing a mutated CYP52A12 gene, a homologous gene or a variant thereof by directed evolution of the CYP52A12 gene in the long-chain dibasic acid synthesis pathway; culturing the strain to produce the long-chain dibasic acid by fermentation; optionally, further comprising the steps of isolating, extracting and/or purifying the long-chain dibasic acid from the culture product;

wherein, the mutated CYP52A12 gene, homologous gene or variant thereof, which, relative to GenBank Accession Number AY230498 and taking the first base upstream of the start codon ATG (in which the "A" is 1) as −1, comprises any one or a combination of some of the following base mutations occurred in the promoter region thereof: −876A>G; −853A>T; −831delT; −825C>A; −823delG; −579A>G; −412_−411AC>TT; −402insTT; −15_1 ACCAACCAACCAACCA (SEQ ID NO.: 37)>ACCAACCAACCA (SEQ ID NO.: 38) (e.g. −7_−4delACCA); and the variant has at least 70% sequence identity to the mutated CYP52A12 gene or homologous gene thereof.

Preferably, the mutated CYP52A12 gene, homologous gene or variant thereof comprises the base mutation −15_1 ACCAACCAACCAACCA (SEQ ID NO.: 37)>ACCAACCAACCA (SEQ ID NO.: 38) (e.g. −7_−4delACCA) in the promoter region thereof.

Preferably, the mutated CYP52A12 gene, homologous gene or variant thereof comprises the base mutations −412_−411AC>TT; −402insTT and −15_1 ACCAACCAACCAACCA (SEQ ID NO.: 37)>ACCAACCAACCA (SEQ ID NO.: 38) (e.g. −7_−4delACCA) in the promoter region thereof.

Preferably, the mutated CYP52A12 gene, homologous gene or variant thereof comprises the base mutations −579A>G; −412_−411AC>TT; −402insTT and −15_1 ACCAACCAACCAACCA (SEQ ID NO.: 37)>ACCAACCAACCA (SEQ ID NO.: 38) (e.g. −7_−4delACCA) in the promoter region thereof.

Preferably, the mutated CYP52A12 gene, homologous gene or variant thereof comprises the base mutations −831delT; −825C>A; −823delG; −579A>G; −412_−411AC>TT; −402insTT and −15_1 ACCAACCAACCAACCA (SEQ ID NO.: 37)>ACCAACCAACCA (SEQ ID NO.: 38) (e.g. −7_−4delACCA) in the promoter region thereof.

Preferably, the sequence of the mutated CYP52A12 gene is set forth in any of SEQ ID NOs. 16 and 22-26 or a sequence having at least 70% sequence identity thereto, for example at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, or 99.96% sequence identity.

Preferably, the long-chain dibasic acid is selected from C9-C22 long-chain dibasic acids, preferably selected from C9-C18 long-chain dibasic acids, more preferably one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one of C10 to C16 dibasic acids, or at least one of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

Preferably, the chemical formula of the monobasic acid impurity comprises $CH_3—(CH_2)n\text{-}COOH$, where $n \geq 7$, and/or $CH_2OH—(CH_2)n\text{-}COOH$, where $n \geq 7$.

In some embodiments, the microorganism is yeast; more preferably the microorganism is selected from *Candida tropicalis* or *Candida sake*.

In some embodiments, to obtain a long-chain dibasic acid producing microorganism strain with a mutated CYP52A12 gene, a homologous gene or a variant thereof, comprises the following steps:

1) preparing a CYP52A12 gene fragment having a mutation by error-prone PCR;

2) preparing fragments upstream and downstream of the CYP52A12 gene necessary for homologous recombination as templates for homologous recombination with a resistance marker gene, preferably the resistance marker gene is hygromycin B;

3) preparing a complete recombination fragment by PCR overlap extension;

4) introducing the recombination fragment into a strain by homologous recombination;

5) screening positive strains by means of the resistance marker;

6) screening strains wherein the content of monobasic acid impurity in the fermentation broth after fermentation is significantly reduced;

7) optionally, removing the resistance marker in the screened strains by further homologous recombination.

Preferably, in the present invention, the existing *Candida tropicalis* strain CATN145 (Deposit No. CCTCC M2011192) is used as the starting strain, hereinafter referred to as CCTCC M2011192, and error-prone PCR method is used to randomly mutate the CYP52A12 gene. The gene is subjected to directed evolution by homologous recombination method to screen for a long-chain dibasic acid producing strain with significantly reduced content of impurity during the production of dibasic acid, wherein the impurity is monobasic acid impurity.

By screening, the present invention obtains a strain in which the content of monobasic acid impurity in the fermentation product is significantly reduced, and is named as mutant strain 430. By sequencing analysis, it is found that, compared to parental strain CCTCC M2011192 and taking the first base upstream of the start codon ATG (wherein "A" is 1) as −1, following base mutations occurred in the promoter region of the CYP52A12 gene of the mutant strain of *Candida tropicalis* screened in the invention: −876A>G, −853A>T, −831delT, −825C>A, −823delG, −579A>G, −412_−411AC>TT, −402insTT, and −15_1 ACCAACCAACCAACCA (SEQ ID NO.: 37)>ACCAACCAACCA (SEQ ID NO.: 38) (e.g. −7_−4delACCA). A promoter sequence containing different combinations of mutation sites was synthesized by the method of whole-genome synthesis (Sangon) (Genbank Accession No. AY230498), comprising 912 bp upstream of the start codon and adjacent 23 bp CDS sequence. Taking the first base upstream of the start codon ATG as −1, any one or combination of several of the above base mutation sites can also achieve the effect of significantly decreased content of monobasic acid impurity.

According to the present invention, the sequence of the *Candida tropicalis* CYP52A12 gene is set forth in SEQ ID NO: 16.

After further removing the resistance marker from the mutant strain, compared to the original strain, the mass ratio of monobasic acid impurity in the fermentation broth after fermentation is significantly reduced, and the content of monobasic acid impurity in the long-chain dibasic acid product obtained after extracting and purifying the fermentation broth can be reduced to 200 ppm or less, particularly during fermentation production of long-chain dodecanedioic acid.

The present invention screens a strain which has base mutations in the promoter region of the CYP52A12 gene by directed evolution of said gene, and the content of monobasic acid impurity in the fermentation broth is significant reduced for different fermentation substrates. After extraction and purification, compared to the parental strain, the content of monobasic acid impurity is decreased by nearly 50%, further improving the purity of the fermentation product long-chain dibasic acid, making the dibasic acid product which is used as important raw materials for nylon filament, engineering plastic, synthetic fragrance, cold-resistant plasticizer, advanced lubricants and polyamide hot melt adhesives, favorable for the production of and the quality improvement of downstream products. More importantly, this greatly reduces the difficulty of the extraction and purification processes at later stages of dibasic acid production, simplifies the process and saves energy.

BRIEF DESCRIPTION OF THE FIGURES

FIG. 2 is the alignment of the nucleotide sequences of the CYP52A12 genes of the mutant strain of the invention (SEQ ID NO: 16) and the original strain (nucleotides 265-1176 of SEQ ID NO: 21), and the mutation sites are boxed with a black box, wherein 192 refers to CCTCC M2011192.

DETAILED DESCRIPTION

Definition

Figure 1:
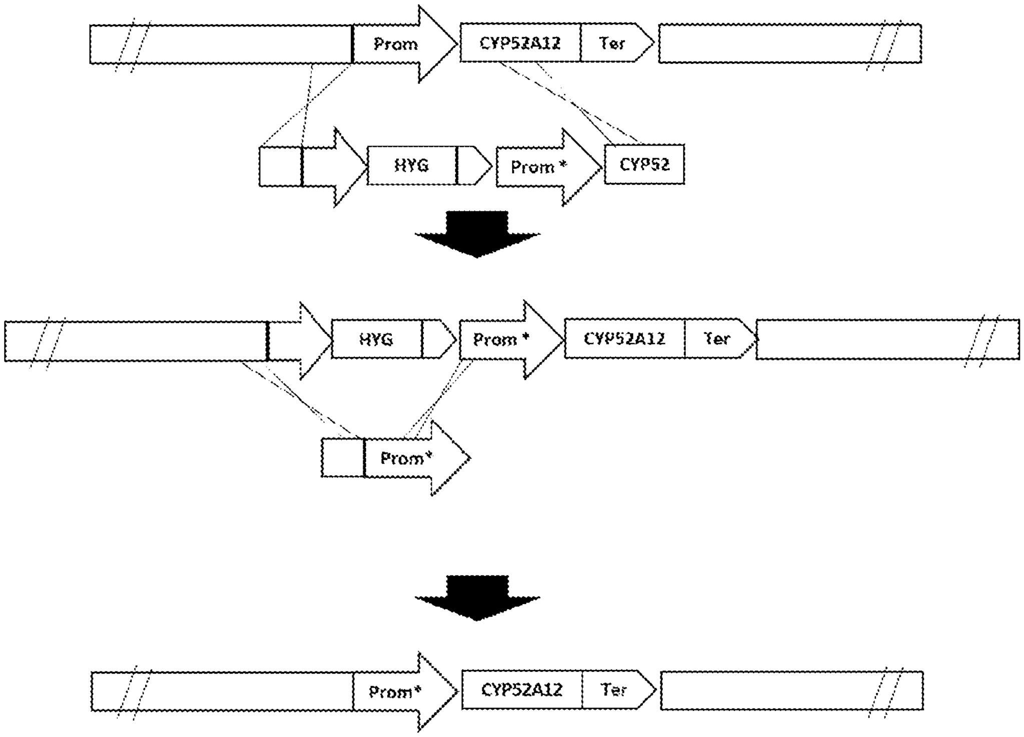
FIG. 1 is a scheme of the integration of the CYP52A12 gene with mutations and the removal of the hygromycin resistance marker by homologous recombination. "*" indicates the mutations that may be present in any region of CYP52A12 (including the promoter, coding region, and terminator).

Long chain alkane: the fermentation substrate of the invention comprises a long chain alkane, belonging to a saturated aliphatic hydrocarbon, which is a saturated hydrocarbon among hydrocarbons; its whole structure is mostly composed only of carbon, hydrogen, carbon-carbon single bond, and carbon-hydrogen single bond. It includes an alkane of the formula $CH_3(CH_2)nCH_3$, where n≥7. Preferred are n-C9-C22 alkanes, more preferred are n-C9-C18 alkanes, and most preferred are n-C10, C11, C12, C13, C14, C15 or C16 alkanes.

Long-chain dibasic acid (LCDA; also known as long chain dicarboxylic acid or long chain diacid, hereinafter abbreviated as dibasic acid sometimes) includes a diacid of the formula $HOOC(CH_2)nCOOH$, where n≥7. Preferably, the long-chain dibasic acid selected from C9-C22 long-chain dibasic acids, preferably selected from C9-C18 long-chain dibasic acids; more preferably comprises one or more of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, preferably at least one or more of n-C10 to C16 dibasic acids, e.g. at least one or more selected from the group consisting of sebacic acid, undecanedioic acid, dodecanedioic acid, tridecanedioic acid, tetradecanedioic acid, pentadecanedioic acid and hexadecanedioic acid.

Long-chain dibasic acid producing microorganism: the strain that has been reported to produce and accumulate a dibasic acid includes bacterium, yeast, and mold, such as *Corynebacterium, Geotrichum candidum, Candida, Pichia, Rhodotroula, Saccharomyces, Yarrowia*, and the like. Among them, many species of *Candida* are good strains for the production of a dibasic acid by fermentation. The strain for fermentation preferably includes: *Candida tropicalis* or *Candida sake.*

In the process of producing a long-chain dibasic acid by fermentation of a long-chain alkane substrate, alkane is oxidized to carboxylic acid containing only one carboxyl group. If the fermentation reaction is not complete, carboxylic acid with only one carboxyl group remains in the fermentation broth as impurity. Because of its extremely similar properties to the long-chain dibasic acid, it is difficult to isolate efficiently by conventional means. Such impurity will enter the final dibasic acid product along with the subsequent treatment process, greatly affecting the purity and quality of the product.

The monobasic acid impurity of the invention refers particularly to a long-chain monocarboxylic acid impurity, which contains only one carboxyl group (—COOH), particularly terminal carboxyl group, in the carboxylic acid molecule. Preferably, the monobasic acid impurity comprises, but not limited to, a long-chain monobasic acid with the number of carbon atoms in the carbon chain being greater than 9, wherein the chemical formula of the monobasic acid impurity comprises $CH_3$—$(CH_2)$n-COOH, where n≥7, and/or $CH_2OH$—$(CH_2)$n-COOH, where n≥7.

Preferably, the monobasic acid impurity is any one or more of a monobasic acid having 9 carbon atoms, a monobasic acid having 10 carbon atoms, a monobasic acid having 11 carbon atoms, a monobasic acid having 12 carbon atoms, a monobasic acid having 13 carbon atoms, a monobasic acid having 14 carbon atoms, a monobasic acid having 15 carbon atoms, a monobasic acid having 16 carbon atoms, a monobasic acid having 17 carbon atoms, a monobasic acid having 18 carbon atoms, and a monobasic acid having 19 carbon atoms. The long-chain monobasic acid refers to a linear monobasic acid containing one terminal carboxyl group, e.g. a monobasic acid having 9 carbon atoms refers to a long-chain monobasic acid containing 9 carbon atoms and having one terminal carboxyl group.

As used herein, the expression "substantially or significantly decreased content of monobasic acid impurity" refers to that, compared to a reference, the content of the fatty acid impurity (e.g. the total content of monobasic acids $CH_3$—

$(CH_2)n$-COOH and $CH_2OH$—$(CH_2)n$-COOH) is decreased by at least 5%, 6%, 7%, 8%, 9%, 10%, 12%, 14%, 16%, 18%, 20%, 25%, 30%, 35% 40%, 50%, 60%, 70%, 80%, 90%, 95% or more, preferably at least 10%, more preferably at least 20%, more preferably at least 40%, more preferably at least 50%, more preferably at least 70% or more.

When a long-chain dibasic acid is produced by fermentation according to the present invention, the fermentation broth after fermentation contains a monobasic acid impurity, and the content of the monobasic acid impurity is significantly reduced relative to the content of the monobasic acid impurity produced by a conventional microbiological fermentation, such as the fermentation by a non-mutant microorganism described in the present invention, such as by at least 5%, 6%, 7%, 8%, 9%, 10%, 12%, 14%, 16%, 18%, 20%, 25%, 30%, 35%, 40%, 50%, 60%, 70%, 80%, 90%, 95% or more, preferably at least 10%, more preferably at least 20%, more preferably at least 40%, more preferably at least 50%, more preferably at least 70% or more.

In some embodiments, the long-chain dibasic acid is produced by a microbiological fermentation, and the fermentation broth contains a monobasic acid impurity, and the content of the monobasic acid impurity is reduced to below 5.0%, such as below 4.0%, 3.0%, 2.0%, 1.5%, 1.4%, 1.3%, 1.2%, 1.1%, 1.0.%, 0.9%, 0.8%, 0.7%, 0.6% or lower, wherein the mass ratio is a mass percentage of the monobasic acid impurity to the long-chain dibasic acid in the fermentation broth, preferably reduced to below 1.5%, more preferably reduced to below 1.0%, and more preferably reduced to below 0.9%.

The long-chain dibasic acid produced by the microbiological fermentation method of the present invention contains a monobasic acid impurity, and the content of the monobasic acid impurity is greater than 0 and less than 15,000 ppm, preferably less than 10,000 ppm, less than 7,000 ppm, less than 5,000 ppm, less than 3,000 ppm, less than 2,000 ppm, less than 1,000 ppm, less than 500 ppm, less than 300 ppm, less than 250 ppm, less than 200 ppm, less than 150 ppm, less than 100 ppm or less.

The unit ppm of the impurity content of the present invention is the mass ratio of the impurity to the long-chain dibasic acid, and 100 ppm=$100*10^{-6}$=0.01%.

In some embodiments, the impurity of DC16 is higher than that of DC12 or DC10 on the whole, such as by at least 10%, at least 20%, at least 30%, at least 40%, at least 50%, 60%, at least 80%, at least 100% or higher, wherein DC refers to long-chain dibasic acid.

In an embodiment of the present invention, when the C12 dibasic acid such as dodecanedioic acid is produced by the microbiological fermentation method of the invention, the monobasic acid impurity is predominantly a monobasic acid impurity having 12 carbon atoms, and the content of the monobasic acid impurity having 12 carbon atoms is less than 8,000 ppm, such as less than 6,000 ppm, 5,000 ppm, 4,000 ppm, 3,000 ppm, preferably less than 2,000 ppm, 1,900 ppm, 1,850 ppm, 1,800 ppm, 1,750 ppm, 1,700 ppm, 1,650 ppm, 1,600 ppm, 1,550 ppm, 1,500 ppm, 1,450 ppm, 1,400 ppm, 1,350 ppm, 1,300 ppm, 1,250 ppm, 1,200 ppm, 1,150 ppm, 1,100 ppm, 1,050 ppm, 1,000 ppm, 950 ppm, 900 ppm, 850 ppm, 800 ppm, 750 ppm, 700 ppm, 650 ppm, 600 ppm, 550 ppm, 500 ppm, 450 ppm, 400 ppm, 350 ppm, 300 ppm, 250 ppm, 200 ppm, 150 ppm, 100 ppm, or less. The chemical formula of the monobasic acid impurity having 12 carbon atoms comprises $CH_3$—$(CH_2)_{10}$—COOH and/or $CH_2OH$—$(CH_2)_{10}$—COOH.

In an embodiment of the present invention, when the C10 dibasic acid such as decanedioic acid is produced by the microbiological fermentation method of the invention, the monobasic acid impurity is predominantly a monobasic acid impurity having 10 carbon atoms, and the content of the monobasic acid impurity having 10 carbon atoms is less than 2,000 ppm, such as less than 2,000 ppm, 1,500 ppm, preferably less than 1,000 ppm, 500 ppm, 300 ppm, 250 ppm, 200 ppm, 150 ppm or less. The chemical formula of the monobasic acid impurity having 10 carbon atoms comprises $CH_3$—$(CH_2)_8$—COOH and/or $CH_2OH$—$(CH_2)_8$—COOH.

In an embodiment of the present invention, when the C16 dibasic acid such as hexadecanedioic acid is produced by the microbiological fermentation method of the invention, the monobasic acid impurity is predominantly a monobasic acid impurity having 16 carbon atoms, and the content of the monobasic acid impurity having 16 carbon atoms is less than 12,000 ppm, such as less than 10,000 ppm, 9,000 ppm, 8,000 ppm, 7,000 ppm, preferably less than 6,000 ppm, or less than 4,000 ppm, or less than 3,500 ppm, 3,000 ppm, 2,000 ppm, 1,000 ppm, 900 ppm, 800 ppm, 700 ppm, 600 ppm, 500 ppm, 400 ppm, 300 ppm, 200 ppm, 150 ppm, or less. The chemical formula of the monobasic acid impurity having 16 carbon atoms comprises $CH_3$—$(CH_2)_{14}$—COOH and/or $CH_2OH$—$(CH_2)_{14}$—COOH.

In some embodiments, the content of monobasic acid impurity according to the invention refers to the total content of monobasic acids $CH_3$—$(CH_2)n$-COOH and $CH_2OH$—$(CH_2)n$-COOH.

The test method for the dibasic acid and the impurity content may employ the techniques well known to those skilled in the art, such as an internal standard method or a normalization method of gas chromatography detection.

CYP52A12 refers to one of the cytochrome oxidase P450 family CYP52 subfamily, which forms a complex with cytochrome reductase CPR and participates in the ω-oxidation of alkanes and lipids during fermentation production of acid. It is known to those skilled in the art that the CYP52A12 gene or homologous gene thereof is also present in other microorganisms producing a long-chain dibasic acid, and their sequences may differ, but are also within the scope of the present invention.

The term "isolated", when applied to a nucleic acid or protein, means that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography.

As used herein, the expression "relative to the GenBank Accession Number AY230498" or "relative to the nucleotide sequence of SEQ ID NO: 21" refers to a mutation at a corresponding position when aligned with the sequence of AY230498 or SEQ ID NO: 21. The corresponding position refers to the numbering of the residue of the reference sequence (SEQ ID NO: 21) when the given polynucleotide sequence (e.g. a mutated CYP52A12 gene sequence) is compared to the reference sequence. A base in a nucleic acid "corresponds" to a given base when it occupies the same essential structural position within the nucleic acid as the given base. In general, to identify corresponding positions, the sequences of nucleic acids are aligned so that the highest order match is obtained (see, e.g. Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994;

Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48: 1073). Alignment of nucleotide sequences also can take into account conservative differences and/or frequent substitutions in nucleotides. Conservative differences are those that preserve the physico-chemical properties of the residues involved. Alignments can be global (alignment of the compared sequences over the entire length of the sequences and including all residues) or local (alignment of a portion of the sequences that includes only the most similar region(s)).

As used herein, the base mutation "XXX N0>N1" means that the base NO at position XXX is mutated to the base N1; "XXXdelN" means that the base N at position XXX is deleted; "XXXinasN0N1" means insertion of N0N1 after position XXX; "XXX0_XXX1 N0N1>N2N3" means the bases N0N1 at positions XXX0 to XXX1 are mutated to N2N3; and "XXX0_XXX1 delN0N1N2N3" means the bases N0N1N2N3 at portions XXX0 to XXX1 are deleted.

For example, taking the first base upstream of the start codon ATG (wherein "A" is position 1) as −1, i.e. the first base immediately adjacent to the based "A" of the start codon "ATG" as −1, base mutation −876A>G means the base "A" at position −976 is mutated to "G", "−831delT" means the base "T" at position −831 is deleted, "−412_−411AC>TT" means the bases "AC" at positions −412 and −411 are mutated to "TT", −402insTT means bases "TT" are inserted after position −402 (i.e. between positions −402 and −403), and "−15_1 ACCAACCAACCAACCA (SEQ ID NO.: 37)>ACCAACCAACCA" (SEQ ID NO.: 38) means the bases "ACCAACCAACCAACCA" (SEQ ID NO.: 37) at positions −15 to 1 are mutated to "ACCAACCAACCA (SEQ ID NO.: 38).

In an embodiment, the sequence of the CYP52A12 gene according to the invention is set forth in SEQ ID NO: 21, wherein the protein coding sequences are the nucleotides 1177 to 2748. Correspondingly, the mutation "−876A>G" correspond to that the nucleotide "A" at position 301 of SEQ ID NO: 21 is mutated to "G"; the mutation "−831delT" correspond to that the nucleotide "T" at position 346 of SEQ ID NO: 21 is deleted; the mutation "−412_−411AC>TT" correspond to that the nucleotides "AC" at positions 765 and 766 of SEQ ID NO: 21 is mutated to "TT"; the mutation "−402insTT" correspond to the insertion of nucleotides "TT" between the positions 774 and 775 of SEQ ID NO: 21; and the mutation "−15_1 ACCAACCAACCAACCA (SEQ ID NO.: 37)>ACCAACCAACCA (SEQ ID NO.: 38)" correspond to that the nucleotides "ACCAACCAACCAACCA" (SEQ ID NO.: 37) at positions 1162-1177 of SEQ ID NO: 21 is mutated to "ACCAACCAACCA (SEQ ID NO.: 38) Herein, where a base is mentioned, G refers to guanine, T refers to thymine, A refers to adenine, C refers to cytosine, and U refers to uracil.

As used herein, the "non-mutated CYP52A12 gene" refers to a CYP52A12 gene that does not comprises the mutation −876A>G; −853A>T; −831delT; −825C>A; −823delG; −579A>G; −412_−411AC>TT; −402insTT or −15_1 ACCAACCAACCAACCA (SEQ ID NO.: 37)>ACCAACCAACCA (SEQ ID NO.: 38 (e.g. −7_−4delACCA) according to the invention, e.g. a naturally occurring wild type allele, such as the CYP52A12 gene with the Accession Number AY230498 in the GenBank. An example of non-mutated CYP52A12 gene is set forth in SEQ ID NO: 21. The non-mutated CYP52A12 gene may contain other mutations, such as a silent mutation in the coding region which does not result in the alteration of the encoded amino acid.

As used herein, "non-mutant microorganism" refers to a microorganism which does not contain the mutated CYP52A12 gene or homologous gene thereof according to the invention, e.g. contain only the CYP52A12 gene with the Accession Number AY230498 in the GenBank. In an embodiment, the non-mutant microorganism contains a non-mutated CYP52A12 gene according to the invention.

Using the method of the present invention, the present invention screens a strain having a mutated CYP52A12 gene, wherein, taking the first base upstream of the start codon ATG (wherein the "A" is portion 1) as −1, any one or a combination of several of the following base mutations occurred in its promoter region: −876A>G; −853A>T; −831delT; −825C>A; −823delG; −579A>G; −412_−411AC>TT; −402insTT; −15_1 ACCAACCAACCAACCA (SEQ ID NO.: 37)>ACCAACCAACCA (SEQ ID NO.: 38) (e.g. −7_−4delACCA).

Homologous genes refer to two or more gene sequences with at least 80% similarity, including orthologous genes, paralogous genes and/or xenologous genes. The homologous gene of the CYP52A12 gene in the invention refers to either the orthologous gene of the CYP52A12 gene, or paralogous gene or xenologous gene of the CYP52A12 gene.

Sequence identity refers to the percent identity of the residues of a polynucleotide sequence variant with a non-variant sequence after sequence alignment and introduction of gaps. In some embodiments, the polynucleotide variant has at least about 70%, at least about 75%, at least about 80%, at least about 90%, at least about 95%, at least about 96%, at least about 97%, at least about 98%, at least about 99%, at least about 99.1%, at least about 99.2%, at least about 99.3%, 99.4%, at least about 99.5%, at least about 99.6%, 99.7%, at least about 99.8%, at least about 99.9%, at least about 99.91%, at least about 99.92%, at least about 99.93%, at least about 99.94%, at least about 99.95%, or at least about 99.96% polynucleotide or polypeptide homology with the polynucleotide described herein.

As used herein, the terms "homology" and "identity" are used interchangeably herein to refer to the extent of non-variance of nucleotide sequences, which can be detected through the number of identical nucleotide bases by aligning a polynucleotide with a reference polynucleotide. The sequence identity can be determined by standard alignment algorithm programs used with default gap penalties established by each supplier. Homologous nucleic acid molecules refer to a pre-determined number of identical or homologous nucleotides. Homology includes substitutions that do not change the encoded amino acid ("silent substitution") as well as identical residues. Substantially homologous nucleic acid molecules hybridize typically at moderate stringency or high stringency all along the length of the nucleic acid or along at least about 70%, 80% or 90% of the full-length nucleic acid molecule of interest. Nucleic acid molecules that contain degenerate codons in place of codons in the hybridizing nucleic acid molecule are also contemplated in the invention. Whether any two nucleic acid molecules have nucleotide sequences that are at least 80%, 85%, 90%, 95%, 96%, 97%, 98% or 99% "identical" can be determined using a known computer algorithm such as the BLASTN, FASTA, DNAStar and Gap (University of Wisconsin Genetics Computer Group (UWG), Madison Wis., USA). Percent homology or identity of nucleic acid molecules can be determined, e.g. by comparing sequence information using a GAP computer program (e.g., Needleman et al. J. Mol. Biol. 48: 443 (1970), as revised by Smith and Waterman (Adv. Appl. Math. 2: 482 (1981)). Briefly, a GAP program defines similarity as the number of aligned symbols (i.e., nucleotides) which are similar, divided by the total number of symbols in the shorter of the two sequences.

Directed evolution refers to a process of simulating a natural selection by technology means. Through an artificially created mutation and specific screening pressure, a protein or nucleic acid is mutated in a specific direction, thereby realizing an evolutionary process in nature that requires thousands of years to complete in a short period of time at the molecular level. The methods for performing directed evolution are known in the art, e.g. error-prone PCR (e.g. Technique, 1, 11-15, 1989; Genome Research, 2, 28-33, 1992).

In some embodiments, in the error-prone PCR of the invention, the concentration of $Mg^{2+}$ is in a range of 1 to 10 mM, preferably 2 to 8 mM, more preferably 5 to 6 mM, and/or the concentration of dNTP is from 0.1 to 5 mM, preferably from 0.2 to 3 mM, more preferably 0.5 to 2 mM, and more preferably from 0.8 to 1.5 mM, for example 1 mM, and/or addition of freshly prepared $MnCl_2$ to a final concentration of 0.1 to 5 mM, preferably 0.2 to 2 mM, more preferably 0.3 to 1 mM, and more preferably 0.4 to 0.7 mM, such as 0.5 mM. In some embodiments, the rate of mutation is increased by decreasing the amount of template and appropriately increasing PCR cycles to 40 or more, e.g. 41, 42, 43, 44, 45, 46, 47, 48, 49, 50, 55, 60 or more.

PCR overlap extension, also known as SOE (gene splicing by overlap extension) PCR, refers to a method of splicing different DNA fragments together via PCR amplification by designing primers having complementary ends.

Homologous recombination refers to the recombination between DNA molecules that relies on sequence similarity, most commonly found within cells to repair mutations that occur during mitosis. Homologous recombination technology has been widely used in genome editing, including gene knockout, gene repair and introduction of a new gene to a specific site. A class of microorganisms represented by *Saccharomyces cerevisiae* has a very high rate of homologous recombination within cells which does not depend on sequence specificity and is obviously advantageous in genome editing. Site-specific recombination relies on the participation of specific sites and site-specific recombinases, and the recombination occurs only between specific sites, such as Cre/loxP, FLP/FRT, and the like. The homologous recombination technology used in the invention does not belong to site-specific recombination, and recombination relies on the intracellular DNA repair system.

The resistance marker refers to a type of selective markers that often has the ability of conferring a transformant survival in the presence of an antibiotic. The resistance marker gene includes NPT, HYG, BLA and CAT, etc., which are resistant to kanamycin, hygromycin, ampicillin/carbenicillin, and chloramphenicol, respectively. Preferably, the resistance marker gene is the hygromycin B resistance gene HYG.

During fermentation, the fermentation medium comprises a carbon source, a nitrogen source, an inorganic salt and a nutritional factor.

In some embodiments, the carbon source comprises one or more selected from the group consisting of glucose, sucrose and maltose; and/or the carbon source is added in an amount of 1% to 10% (w/v), such as 1.5%, 2.0%, 2.5%, 3.0%, 3.5%, 4.0%, 4.5%, 5.0%, 6.0%, 7.0%, 8.0%, or 9.0%.

In some embodiments, the nitrogen source comprises one or more selected from the group consisting of peptone, yeast extract, corn syrup, ammonium sulfate, urea, and potassium nitrate; and/or the nitrogen source is added in a total amount of 0.1%-3% (w/v), such as 0.2%, 0.4%, 0.5%, 0.6%, 0.8%, 1.0%, 1.2%, 1.5%, 1.8%, 2.0%, or 2.5%.

In some embodiments, the inorganic salt comprises one or more selected from the group consisting of potassium dihydrogen phosphate, potassium chloride, magnesium sulfate, calcium chloride, ferric chloride, and copper sulfate; and/or the inorganic salt is added in a total amount of 0.1%-1.5% (w/v), such as 0.2%, 0.3%, 0.4%, 0.5%, 0.6%, 0.7%, 0.8%, 0.9%, 1.0%, 1.1%, 1.2%, 1.3%, or 1.4%.

In some embodiments, the nutritional factor comprises one or more selected from the group consisting of vitamin B1, vitamin B2, vitamin C, and biotin; and/or the nutritional factor is added in a total amount of 0-1% (w/v), such as 0.2%, 0.3%, 0.4%, 0.5%, 0.6%, 0.7%, 0.8%, or 0.9%. According to common knowledge in the art of fermentation, the percentage in the invention is the mass to volume ratio, i.e. w/v; and % indicates g/100 mL.

Those skilled in the art can easily determine the amount of the above substances to be added.

In one embodiment of the invention, the inoculation amount of the strain for fermentation is 10% to 30%, for example 11%, 12%, 13%, 14%, 15%, 16%, 17%, 18%, 19%, 20%, 22%, 24%, 25%, 27%, or 29%. When the strain is cultured to an optical density ($OD_{620}$) of 0.5 or more (diluted 30 folds), the substrate is added for fermentation conversion.

Extraction and purification of a long-chain dibasic acid: the fermentation broth containing a salt of a long-chain dibasic acid obtained by fermentation is subjected to extraction and purification treatment to obtain a long-chain dibasic acid product. The step of extraction and purification comprises: sterilization of fermentation broth, and acidification, solid-liquid separation, and/or solvent crystallization of the obtained clear solution. Some of fermentation broth may contain a salt of a long-chain dibasic acid.

The extraction and purification according to the present invention may be repeated more than once, and performing multiple extraction and purification steps contribute to further reducing the impurity content in the dibasic acid product. For example, in one embodiment of the present invention, with reference to the refining process in Example 1 of Chinese Patent Application CN 101985416 A, the long-chain dodecanedioic acid product obtained by the present invention is further treated, and the content of the monobasic acid impurity having 12 carbon atoms in the obtained long-chain dodecanedioic acid can be reduced from greater than 5000 ppm before treatment to less than 4,000 ppm, for example, less than 3000 ppm, less than 2000 ppm, less than 1000 ppm, less than 500 ppm, less than 400 ppm, less than 300 ppm, or even less than 250 ppm, 200 ppm, 150 ppm or 100 ppm.

The fermentation broth containing a salt of a long-chain dibasic acid refers to a fermentation broth containing a salt of the long-chain dibasic acid produced during the biological fermentation for producing the long-chain dibasic acid. The fermentation broth containing a salt of a long-chain dibasic acid may contain sodium salt, potassium salt or ammonium salt of the long-chain dibasic acid.

The sterilization is preferably membrane filtration: the residual bacteria and large proteins are separated by using a filtration membrane, and are effectively separated from the fermentation broth containing the salt of the long-chain dibasic acid. Further, the ceramic membrane filtration process is preferred. When membrane filtration is carried out using a ceramic membrane, it is preferred that the pre-membrane pressure is 0.2 to 0.4 MPa; preferably, the pore size of the filtration membrane is 0.05 to 0.2 μm.

The acidification is a treatment of acidifying the obtained membrane clear liquid containing a salt of a long-chain dibasic acid after membrane filtration, and the salt of the long-chain dibasic acid is converted into a long-chain dibasic acid precipitate by adding an acid. It is preferred to use an inorganic acid such as sulfuric acid, hydrochloric acid, nitric acid, or mixture thereof for acidification. The inorganic acid during the acidification treatment is added in an amount sufficient to precipitate the long-chain dibasic acid in the solution, mainly based on the endpoint pH of the solution, preferably the acidification end point pH is lower than 5, and more preferably lower than 4.0. When an inorganic acid is added for acidification, the long-chain dibasic acid precipitate and corresponding inorganic salt solution can be obtained. The membrane clear liquid refers to the liquid obtained after membrane filtration by a membrane.

The solid-liquid separation is to separate the obtained long-chain dibasic acid precipitate from the acidified mother liquid, and the solid-liquid separation includes filtration or/and centrifugation, and a commonly used solid-liquid separation device can be used.

Preferably, the step of extraction and purification further comprises decolorization of the fermentation broth containing a long-chain dibasic acid salt, adding activated carbon to the fermentation broth or the membrane clear liquid containing the salt of the long-chain dibasic acid for decolorization treatment, and removing the activated carbon by filtration after decolorization treatment. Decolorization step can further remove impurities in the long-chain dibasic acid solution. Preferably, the amount of activated carbon added is 0.1-5 wt %, preferably 1-3 wt % (relative to the amount of the long-chain dibasic acid contained in the solution).

The solvent crystallization, i.e., dissolving a long-chain dibasic acid precipitate in an organic solvent, and crystallizing the long-chain dibasic acid by cooling, evaporation, and separating-out, and isolating the crystal to obtain a purified long-chain dibasic acid. The organic solvent comprises one or more of alcohol, acid, ketone and ester; wherein the alcohol comprises one or more of methanol, ethanol, isopropanol, n-propanol and n-butanol; the acid comprises acetic acid; the ketone comprises acetone; and the ester comprises ethyl acetate and/or butyl acetate.

In another preferred embodiment, the long-chain dibasic acid precipitate is dissolved in an organic solvent, and then decolorized, and then separated to obtain a clear solution. When decolorized with activated carbon, the decolorization temperature is 85 to 100° C., and the decolorization time is 15 to 165 min. In another preferred embodiment, after separating the clear liquid, cooling and crystallizing is carried out, and cooling and crystallizing may include the steps of: first cooling to 65-80° C., incubating for 1 to 2 hours, then cooling to 25-35° C., and crystallizing. In another preferred embodiment, after crystallization, the resulting crystal is separated, thereby obtaining the long-chain dibasic acid, and the crystal may be separated by centrifugation.

In some embodiments, the present invention relates to the production of nylon filaments, engineering plastics, synthetic fragrances, cold-resistant plasticizers, advanced lubricating oils, and polyamide hot melt adhesives using the dibasic acid products obtained above.

As used herein, "optional" or "optionally" means that the subsequently described event or circumstance does or does not occur, and that the description comprises instances where the event or circumstance occurs or does not occur. For example, "optionally a step" means that the step is present or not present.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value.

The invention will be further illustrated by the following non-limiting examples. Those skilled in the art will recognize that modifications can be made to the invention without departing from the spirit thereof, and such modifications also fall within the scope of the invention.

The following experimental methods are all conventional methods unless otherwise specified, and the experimental materials used can be easily obtained from commercial companies unless otherwise specified.

Example 1 Culture Media, Culture Methods and Dibasic Acid Detection Method in the Examples 1. the formulation of YPD medium (w/v): 2% peptone, 2% glucose and 1% yeast extract (OXOID, LP0021). 1.5-2% agar powder was added to form a solid medium.

During culturing, a single colony was picked into a 2 mL centrifuge tube containing 1 mL YPD liquid medium, incubated at 30° C. on a shaker at 250 RPM for 1 day.

2. the formulation of seed medium (w/v): sucrose 10-20 g/L (specifically used, 10 g/L), yeast extract 3-8 g/L (specifically used, 3 g/L), industrial fermentation corn syrup (corn syrup for short, with total nitrogen content of 2.5 wt %) 2-4 g/L (specifically used, 2 g/L), $KH_2PO_4$ 4-12 g/L (specifically used, 4 g/L), urea 0.5-4 g/L (specifically used, 0.5 g/L) (separately sterilized at 115° C. for 20 min), and the fermentation substrate was n-dodecane, n-decane, and n-hexadecane, at 20 mL/L, respectively.

During culturing, the cultured bacterial solution obtained in step 1 was inoculated into a 500 mL shake flask containing 30 mL seed medium. The bacterial solution was inoculated in an amount of 3-5% and incubated at 30° C. on a shaker at 250 RPM until $OD_{620}$ reached 0.8 (30-fold dilution).

3. Fermentation medium (w/v): sucrose 10-40 g/L (specifically used, 10 g/L), corn syrup (total nitrogen content of 2.5 wt %) 1-5 g/L (specifically used, 1 g/L), yeast extract 4-12 g/L (specifically used, 4 g/L), NaCl 0-3 g/L (not used), $KNO_3$ 4-12 g/L (specifically used, 4 g/L), $KH_2PO_4$ 4-12 g/L (specifically used, 4 g/L), urea 0.5-3 g/L (specifically used, 0.5 g/L) (separately sterilized at 115° C. for 20 min), and the fermentation substrate was n-dodecane, n-decane, and n-hexadecane, at 300-400 mL/L (specifically used, 300 mL/L), respectively, and acrylic acid 4 g/L, and 1N HCl and 1N NaOH was used to adjust pH to 7.5-7.6.

In fermentation, the seed solution obtained in step 2 was inoculated into a 500 mL shake flask containing 15 mL fermentation medium. The amount of inoculum is 10-30% and incubated at 30° C. on a shaker at 250 RPM for 90-144h. During culturing, the pH value was adjusted to the specified range by adding acid or base at a certain interval of time.

4. Steps for determining the yield of dibasic acid and the content of monobasic acid impurity by gas chromatography (GC)

(1) Detection of fermentation broth product and impurity content: The fermentation broth was pretreated by conventional gas chromatography and detected by gas chromatography. The chromatographic conditions were as follows:

Column: Supelco SPB-50 30m*0.53 mm*0.5 μm (Cat. No. 54983).

Gas Chromatograph (Shimadzu, GC-2014).

Method: The initial temperature was 100° C., and the temperature was raised to 230° C. at a rate of 15° C./min and kept for 2 min. The carrier gas was hydrogen, the inlet temperature was 280° C., the FID temperature was 280° C., and the injection volume was 4 μL.

The yield of the dibasic acid was calculated based on the ratio of the peak area of the dibasic acid product and the internal standard peak area with a known concentration, and the impurity content was calculated by the ratio of the peak area of the dibasic acid product to the peak area of the impurity.

(2) Determination of purity and impurity content of solid product: the solid product was pretreated by conventional gas chromatography and detected by gas chromatography, Chromatographic conditions: Column: Supelco SPB-50 30 m*0.53 mm*0.5 μm (Cat. No. 54583).

Gas Chromatograph (Shimadzu, GC-2014).

Method: The initial temperature was 100° C., and the temperature was raised to 230° C. at a rate of 15° C./min and kept for 2 min. The carrier gas was hydrogen, the inlet temperature was 280° C., the FID temperature was 280° C., and the injection volume was 4 μL.

The purity of the product and impurity content were calculated from the peak area of the dibasic acid product and the peak area of impurity.

Example 2 Preparation of CYP52A12 Mutation Template

1. Preparation of CYP52A12 Promoter Mutation Template

The genomic DNA of *Candida tropicalis* CCTCC M2011192 was extracted by using Ezup Yeast Genomic DNA Extraction Kit (Sangon, Cat No. 518257). The method with liquid nitrogen grinding was used in favor of increasing the cell wall disruption efficiency. Genomic DNA obtained by this method was used as template for error-prone PCR. The obtained mutation-free product was called CYP52A12 and was confirmed by sequencing to be identical to the sequence set forth by GenBank Accession Number: AY230498.

2. Error-Prone PCR

The concentration of $Mg^{2+}$ was adjusted (2-8 mM, increasing by 0.5 mM) and the promoter of CYP52A12 gene was amplified by error-prone PCR using normal Taq enzyme (Takara, Cat No. R001B). The primers were as follows:

```
                                  (SEQ ID NO. 1)
Pcyp52a12-F: 5'- GTCGACTTCTCCTTTAGGCA-3'

                                  (SEQ ID NO. 2)
Pcyp52a12-R: 5'- TCGATGATTTCTTGTGTGGC-3'
```

PCR reaction conditions were:

Step 1: 98° C. for 30 s,

Step 2: 98° C. for 10 s, 52° C. for 30 s, 72° C. for 1 m, 35 cycles,

Step 3: 72° C. for 5 m.

The PCR product was subjected to 1% agarose gel electrophoresis and recovered and purified by using the Axygen Gel Recovery Kit (Axygen, AP-GX-250G).

Example 3 Preparation of Homologous Recombination Template

All DNA fragments in this example were obtained by amplification using PrimeSTAR® HS High Fidelity DNA polymerase (Takara, R040A). The DNA fragments were subjected to 1% agarose gel electrophoresis, followed by recovery and purification by using the Axygen Gel Recovery Kit.

(1) Amplification of the upstream and downstream homologous recombination fragments. The template was the above genomic DNA of *Candida tropicalis*. The primer sequences were as follows:

```
                                                  (SEQ ID NO. 3)
CYP52A12_Upstream-F: 5'- GGTCGAGGAAGTGGCATTAAA-3'

                                                  (SEQ ID NO. 4)
CYP52A12_Upstream-R: 5'- ACCTCCTGCAGTTGCCAT-3'
```

The PCR reaction conditions were as follows:

Step 1: 98° C. for 30 s,

Step 2: 98° C. for 10 s, 53° C. for 10 s, 72° C. for 30 s, 30 cycles,

Step 3: 72° C. for 5 m.

The resultant product was designated as CYP52A12_Upstream, and verified by sequencing, set forth in SEQ ID NO. 17.

```
                                                  (SEQ ID NO. 5)
CYP52A12_Downstream-F: 5'- ATGGCCACACAAGAAATCAT-3'

                                                  (SEQ ID NO. 6)
CYP52A12_Downstream-R: 5'- AGTCTGGGAGTAACT
TCTGG-3' .
```

The PCR reaction conditions were as follows:

Step 1: 98° C. for 30 s,

Step 2: 98° C. for 10 s, 50° C. for 10 s, 72° C. for 45 s, 30 cycles,

Step 3: 72° C. for 5 m.

The resultant product was designated as CYP52A12_Downstream, and verified by sequencing, the sequence of which was set forth in SEQ ID NO. 18.

(2) Amplification of the resistance screening marker (HYG, hygromycin resistance gene). The amplification template was the vector pCIB2 (SEQ ID NO. 11) owned by our company. The primer sequences were as follows:

```
CYP52A12 HYG-F:
                                                  (SEQ ID NO. 7)
5'-ATGGCAACTGCAGGAGGTGCATGCGAACCCGAAAATGG-3'

CYP52A12 HYG-R:
                                                  (SEQ ID NO. 8)
5'-TGCCTAAAGGAGAAGTCGACGCTAGCAGCTGGATTTCACT-3' .
```

The PCR reaction conditions were as follows:

Step 1: 98° C. for 30 s,

Step 2: 98° C. for 10 s, 55° C. for 10 s, 72° C. for 1 m 50 s, 5 cycles,

Step 3: 98° C. for 10 s, 72° C. for 2 m, 25 cycles,

Step 4: 72° C. for 5 m.

The resultant product, called HYG, was verified by sequencing, as set forth in SEQ ID NO. 9.

(3) PCR overlap extension to obtain a complete recombination template.

The four PCR fragments recovered above were subjected to overlap extension to obtain a homologous recombination template, which was recovered and purified. The specific method was as follows:

Overlap extension PCR was performed by adding an equimolar amount of the fragments CYP52A12_Upstream, Pcyp52a12, HYG and CYP52A12_Downstream as templates, using primers CYP52A12_Upstream-F and CYP52A12_Downstream-R, and using PrimeSTAR® HS High Fidelity DNA polymerase.

The PCR reaction conditions were as follows:

Step 1: 98° C. for 30 s,

Step 2: 98° C. for 10 s, 55° C. for 10 s, 72° C. for 5 m 30 s, 30 cycles,

Step 3: 72° C. for 8 m.

The recombination fragment with a size of approximately 5.1 Kb was recovered and purified after gel electrophoresis.

FIG. 1 is a schematic diagram of the integration of the CYP52A12 gene with a mutation site by the homologous recombination and removal of the hygromycin resistance marker according to the present invention.

Example 4 Construction of *Candida tropicalis* CYP52A12 Gene Mutant Library

1. Preparation of Yeast Electroporation-competent Cells

The yeast cells CCTCC M2011192 subjected to overnight incubation at 30° C. on a shaker at 250 RPM were inoculated into 100 mL of the YPD medium of Example 1 to $OD_{620}$ of 0.1, and cultured under the same conditions to $OD_{620}$ of 1.3. The cells were collected by centrifugation at 3000 g, 4° C. Cells were washed twice with ice-cold sterile water and collected, and then the cells were re-suspended in 10 mL of ice-cold 1M sorbitol solution. The cells were collected by centrifugation at 4° C., 1500 g and re-suspended in 1 mL sorbitol solution above. Aliquots of 1004 of cell suspension were for genetic transformation.

2. Competent Yeast Cell Electroporation

1 μg of the DNA fragments for recombination recovered in step (3) of Example 3 were added to the above competent cells, and placed on ice for 5 min and transferred to a 0.2 cm cuvette, and then performing electroporation (BioRad, Micropulser™ Electroporator, program SC2, 1.5 kV, 25 uFD, 200 ohms). A mixture of 1 mL of YPD and 1M sorbitol (1:1, v/v) was quickly added, and cultured at 30° C., 200 RPM for 2 hours. The bacterial cells were collected and plated on a YPD medium plate with 100 mg/L of hygromycin B, placed still at 30° C. for 2-3 days until single colonies appeared.

Example 5 Screening of Mutant Strains

1. Screening method: single colonies obtained in Example 4 were picked into a 2 mL centrifuge tube with 1 mL YPD medium of Example 1 (containing 100 mg/L hygromycin B), and cultured at 30° C. on a shaker at 250 RPM for 1 day. The above bacterial solution was inoculated into a 500-mL shake flask with 30 mL of the seed medium of Example 1 (containing 100 mg/L hygromycin B). The inoculum amount was 3%, cultured at 250 RPM and 30° C. until $OD_{620}$ reached 0.8 (30-fold dilution). The seed solution was inoculated into a 500-mL shake flask containing 15 mL of the fermentation medium of Example 1, the inoculum amount was 20%, and the substrate was n-dodecane in the fermentation medium. The culture at 250 RPM and 30° C. was continued until the end of the fermentation. The original strain CCTCC M2011192 was used as control: the medium, culture and fermentation methods were the same as above except that the medium did not contain hygromycin B.

0.5 g sample of the above fermentation broth was taken and subjected to GC assay using the method described in Example 1 (4), and the content of C12 dibasic acid content and the mass ratio of the monobasic acid impurity having 12 carbon atoms were calculated.

2. Screening results: a candidate strain with a significant reduction in monobasic acid impurity content compared to the original strain CCTCC M2011192 was screened, designated as 430HYG, and the results were shown in Table 1 below.

TABLE 1

| Strain | Control CCTCC M2011192 | 430 HYG |
|---|---|---|
| Yield of C12 dibasic acid (mg/g) | 148.8 | 149.6 |
| Mass ratio of monobasic acid impurity having 12 carbon atoms (%) | 2.22 | 1.15 |

The mass ratio of the monobasic acid impurity of the present invention was the mass percentage of it to C12 dibasic acid. From Table 1, the mass ratio of the monobasic acid impurity having 12 carbon atoms was decreased by 48.2%.

Example 6 Sequence Analysis of CYP52A12 Gene in the Mutant Strain

1. According to the method of Example 2, the genomic DNAs of the yeast CCTCC M2011192 and 430HYG were extracted, and the promoter region of the CYP52A12 gene was amplified using PrimeSTAR® HS High Fidelity DNA polymerase (Takara). The primers were CYP52A12-F and CYP52A12-R.

The PCR reaction conditions were as follows:

Step 1: 98° C. for 30 s,

Step 2: 98° C. for 10 s, 52° C. for 10 s, 72° C. for 1 m, 30 cycles,

Step 3: 72° C. for 5 m.

2. After completion of the PCR, the product was subject to gel electrophoresis and recovered and purified.

3. Addition of As to the purified PCR fragment: 204 of recovered PCR amplified fragment was added to 4 μL of 10× Takara Taq Buffer, 3.2 μL of dNTP (each 10 mM) and 0.2 μL of Takara Taq, supplemented with $ddH_2O$ to 40 μL, incubated at 72° C. for 20 minutes, and recovered by Axygen PCR purification kit.

4. TA cloning. 4 μL of the PCR fragment recovered after addition of As were added to 1 μL pMD19-T vector backbone and 5 μL Solution I, mixed well and incubated at 16° C. for 30 min. The ligation product was transformed into DH5a chemical competent cells and positive clones were picked and sent to Majorbio for sequencing.

The results showed that: the sequence of the CYP52A12 gene of the parental CCTCC M2011192 was identical to the sequence in the GenBANK database (Accession Number: AY230498), while the mutant strain 430HYG had base mutations in the promoter region. As shown in FIG. 2, several base mutations occurred in the promoter region of CYP52A12 (indicated with black box in the sequence alignment result), the sequence of which was set forth in SEQ ID NO: 16.

Example 7 Removal of the Resistance Marker

1. Preparation of Homologous Recombination Template

The genomic DNA of the *Candida tropicalis* mutant strain 430HYG was used as a template to amplify recombinant template fragments CYP52A-Upstream-2 and Pcyp52a12 necessary for removal of the resistance screening marker, using PrimeSTAR® HS high-fidelity DNA polymerase, and recovered after gel electrophoresis. The sequence obtained was set forth in SEQ ID NOs. 14 and 15. The primer sequences and PCR reaction conditions were as follows:

```
CYP52A12_Upstream-F:
                                   (SEQ ID NO. 3)
5'-GGTCGAGGAAGTGGCATTAAA-3'

CYP52A12_Upstream-2R:
                                  (SEQ ID NO. 10)
TGCCTAAAGGAGAAGTCGACACCTCCTGCAGTTGCCAT-3'

Pcyp52a12-F:
                                   (SEQ ID NO. 1)
5'-GTCGACTTCTCCTTTAGGCA-3'

Pcyp52a12-R:
                                   (SEQ ID NO. 2)
5'-TCGATGATTTCTTGTGTGGC-3'
```

The PCR reaction conditions were as follows:

Step 1: 98° C. for 30 s,

Step 2: 98° C. for 10 s, 52° C. for 10 s, 72° C. for 1 m, 30 cycles,

Step 3: 72° C. for 5 m.

The above PCR fragments were recovered and purified, and equimolar amounts of CYP52A12_Upstream-2 and Pcyp52a12 were added as templates, with the primers of CYP52A12_Upstream-F and Pcyp52a12-R. PCR overlap reaction was carried out with PrimeSTAR® HS high-fidelity DNA polymerase. The PCR conditions were as follows:

Step 1: 98° C. 30 s

Step 2: 98° C. 10 s, 52° C. 10 s, 72° C. 1 m 30 s; 30 cycles

Step 3: 72° C. 5 m.

After gel electrophoresis, a fragment of about 1.3 Kb obtained by the overlap extension was recovered and purified, i.e. a homologous recombination template necessary for the removal of the hygromycin screening marker, the sequence of which was set forth in SEQ ID NO. 12.

2. Removal of the Resistance Marker

Freshly electro-competent cells of the strain 430HYG were prepared and 1 μg of the recombination fragment recovered in step 1 was added. After being placed on ice for 5 min, the cells were quickly transferred to a pre-chilled 0.2 cm cuvette on ice and transformed by electroporation (supra, 1.5 kV, 25 uFD, 200 ohms). A mixture of 1 mL YPD and 1M sorbitol (1:1, v/v) was quickly added, and incubated at 30° C. and 200 RPM for 2 hours. The bacterial cells were collected and plated on an YPD medium plate without an antibiotic, and cultured at 30° C. for 2-3 days until single colonies appeared.

3. Screening for Strains with the Resistance Marker Removed

Single colonies were picked and correspondingly inoculated on YPD plates with and without hygromycin (100 mg/L). Single colonies that could grow on the medium without the antibiotic but could not grow on the medium with the antibiotic were picked and inoculated to a 2 mL centrifuge tube containing 1 mL of the YPD medium, incubated overnight at 4° C. and 250 RPM, and the colony PCR was used to determine whether the resistance screening marker was removed or not in the next day. The DNA polymerase used was Takara Taq, with the primers:

a) CYP52A12_Upstream-F and Pcyp52a12-R,

```
b)        HYG-F:
                                 (SEQ ID NO. 19)
          5'-CTCGGAGGGCGAAGAATCTC-3'

          HYG-R:
                                 (SEQ ID NO. 20)
          5'-CAATGACCGCTGTTATGCGG-3'.
```

The PCR conditions were as follows:

Step 1: 98° C. for 30 s,

Step 2: 98° C. for 10 s, 52° C. for 30 s, 72° C. for 35 s, 30 cycles,

Step 3: 72° C. for 5 min.

4. Screening Results

By colony PCR, one strain with the resistance screening marker removed was screened out, and verified by sequencing that the same mutations were present in the promoter region of the CYP52A12 gene in this strain as the strain 430HYG, and the hygromycin screening marker gene was removed. This strain was eventually designated as 430.

Example 8 Fermentation Production of Long-Chain Dodecanedioic Acid by Strain 430

Fermentation: Strain 430 was inoculated to a 2 mL centrifuge tube containing 1 mL of YPD medium of Example 1, and incubated at 30° C. on a shaker at 250 RPM for 1 day. The above bacterial solution was inoculated into a 500-mL shake flask with 30 mL of the seed medium of Example 1, wherein the inoculation amount was 3%, and cultured at 250 RPM and 30° C. on a shaker until $OD_{620}$ reached 0.8 (after 30-fold dilution). The seed solution was inoculated into a shake flask containing 15 mL of the fermentation medium of Example 1, wherein the inoculation amount was 20%, and the substrate was n-dodecane in the fermentation medium. The culturing on shaker at 250 RPM and 30° C. was continued until the completion of the fermentation. The strain CCTCC M2011192 was used as control, and the medium, culture and fermentation methods were the same as described above.

A 0.5 g sample of the fermentation broth was taken and measured by GC detection using the method described in Example 1 (4), and the yield of C12 dibasic acid and the mass ratio of the monobasic acid impurity having 12 carbon atoms were calculated. The results were shown in Table 2 below.

TABLE 2

| Strain | CCTCC M2011192 | 430 |
|---|---|---|
| Yield of C12 dibasic acid (mg/g) | 150.4 | 151.3 |
| Mass ratio of the monobasic acid impurity having 12 carbon atoms (%) | 2.16 | 1.09 |

It can be seen from Table 2 that the mass ratio of the monobasic acid impurity having 12 carbon atoms was decreased by 49.5% after the removal of the resistance marker.

Extraction and Purification:

(1) The pH of the above fermentation broth was adjusted to 8.5 with 30% (mass concentration) sodium hydroxide solution, the concentration of long-chain dibasic acid was adjusted by adding water to 8.9 wt % and heated to 45° C., and the fermentation broth was filtered with a ceramic membrane with pore size of 0.05 μm (purchased from Suntar Membrane Technology (Xiamen) Co., Ltd.). The area of the ceramic membrane used was 0.84 square meters, and the pre-membrane pressure was set to 0.3 MPa. The membrane clear liquid was collected.

(2) The obtained membrane clear liquid was decolorized by adding 5 wt % of powdered activated carbon (relative to the amount of long-chain dibasic acid contained in the solution) at 60° C., and filtered to obtain a clear liquid.

(3) The clear liquid was further added with sulfuric acid, the pH was adjusted to 3.5, cooled to 30° C., and filtered to obtain a wet solid. The filter cake was washed with pure water the weight of which was 3 times to the wet solid, and filtered and dried to obtain primary C12 dibasic acid product.

(4) Acetic acid at a concentration of 97% whose amount was 3.5 times relative to the weight of the primary C12 dibasic acid product was added to the primary C12 dibasic acid product and heated to 85° C. to dissolve, and 1% macroporous powdered activated carbon (relative to the weight of the primary C12 dibasic acid product) was added for decolorization and kept at 85° C. for 1 hour, and hot-filtered to obtain a clear liquid. The temperature of the solution was reduced at a rate of 10° C./hour to obtain a long-chain dibasic acid crystal solution at 30° C. The solution was filtered and the solvent of the wet solid was washed with water, and dried to obtain secondary C12 dibasic acid product.

(5) Step (4) was repeated on the secondary C12 dibasic acid product to obtain the tertiary C12 dibasic acid product.

The purity of the C12 dibasic acid product and the content of monobasic acid impurity obtained in extraction and purification steps (3)-(5) were determined and calculated using the method described in Example 1 (4), as shown in Table 3 below:

TABLE 3

| Dodecanedioic acid | Strain | CCTCC M2011192 | 430 |
|---|---|---|---|
| Primary product | Purity of C12 dibasic acid (%) | 97.32 | 98.21 |
| | Content of monobasic acid impurity having 12 carbon atoms (ppm) | 11200 | 6400 |
| Secondary product | Purity of C12 dibasic acid (%) | 98.55 | 99.02 |
| | Content of monobasic acid impurity having 12 carbon atoms (ppm) | 740 | 475 |
| Tertiary product | Purity of C12 dibasic acid (%) | 99.72 | 99.85 |
| | Content of monobasic acid impurity having 12 carbon atoms (ppm) | 365 | 165 |

Example 9 To further verify the above mutations, the genomic DNA of yeast 430HYG was extracted, and the DNA fragment containing the mutated CYP52A12 and HYG resistance gene was amplified via PCR using PrimeSTAR® HS high-fidelity DNA polymerase, with the primers CYP52A12_Upstream-F (SEQ ID NO. 3) and Pcyp52a12-R (SEQ ID NO. 2), and the PCR reaction conditions were as follows:

Step 1: 98° C. 30 s

Step 2: 98° C. 10 s, 52° C. 10 s, 72° C. 4 m, 30 cycles

Step 3: 72° C. 5 m.

The fragment with a size of approximately 4 Kb was recovered and purified after gel electrophoresis, and verified by sequencing, the sequence of which was set forth in SEQ ID NO. 13. The process of introducing via homologous recombination the above DNA fragment into the strain CCTCC M2011192 was the same as in Examples 4 and 5, and the sequencing procedure of the promoter of the CYP52A12 gene of the single clone obtained by screening was the same as in Example 6. It was verified by sequencing that the selected single clone was integrated with the CYP52A12 gene with mutations, and the mutation sites were consistent with SEQ ID NO. 16. One of the bacterial strains was named as 431HYG.

The fermentation method was the same as described in Example 5, and the strains used were CCTCC M2011192, 430HYG and 431HYG. After the fermentation, the samples of 0.5 g of the above fermentation broths were taken to calculate the yield of C12 dibasic acid and the content of monobasic acid impurity, as shown in Table 4. The results showed that, consistent with 430HYG, the content of monobasic acid impurity in 431HYG was significantly reduced compared to that of the control CCTCC M2011192.

TABLE 4

| Strain | CCTCC M2011192 | 430HYG | 431HYG |
|---|---|---|---|
| Yield of C12 dibasic acid (mg/g) | 149.8 | 150.2 | 150.1 |
| Mass ratio of monobasic acid impurity having 12 carbon atoms (%) | 2.17 | 1.10 | 1.11 |

Example 10 Determination of the Influence of Different Base Mutation Sites on the Content of Monobasic Acid Impurity 1. Synthesis of the Promoter Sequences Containing Different Combinations of Mutation Sites A promoter sequence containing different combinations of mutation sites (Genbank Accession No. AY230498) was synthesized using the whole-genome synthesis (Sangon) conventionally used in the art, comprising 912 bp upstream of the start codon and adjacent 23 bp CDS sequence. Taking the first base upstream of the start codon as −1, the specific mutation sites were as follows:

Pcyp52a12-1: −7_−4delACCA;

Pcyp52a12-2: −412_−411AC>TT, −402insTT, −7_−4delACCA;

Pcyp52a12-3: −579A>G, −412_−411AC>TT, −402insTT, −7_−4delACCA;

Pcyp52a12-4: −831delT, −825C>A, −823delG, −579A>G, −412_−411AC>TT, −402insTT, −7_−4delACCA (corresponding to −15_1ACCAACCAACCAACCA (SEQ ID NO.: 37)>ACCAACCAACCA). (SEQ ID NO.: 38)

2. Preparation of Homologous Recombination Template

The homologous recombination template was prepared in the same manner as in Example 3 except that the promoter fragment was different. After PCR, the DNA fragment with a size of about 5.1 Kb, i.e. homologous recombination template, was recovered and purified, and verified by sequencing, designated as T12-1, T12-2, T12-3 and T12-4 in the order described in step 1 of Example 10, successively.

3. Construction of Mutant Strains Containing Different Combinations of Mutation Sites in the Promoter Region of CYP52A12

The mutant strains containing different combinations of mutation sites in the CYP52A12 promoter region were constructed by homologous recombination method. The method was the same as in Examples 4 and 5. After 2-3 days, the colonies growing on the plate were picked and identified by colony PCR. The results of the recombination were verified by sequencing. The method was the same as in Example 6. After verification by sequencing, one strain of the obtained mutant strains was randomly selected and designated as P12-1, P12-2, P12-3 and P12-4 in the order described in step 1 of Example 10, respectively.

4. Comparison of Long Chain C12 Dibasic Acids Produced by Fermentation of Different Strains Single colonies of 430HYG, P12-1, P12-2, P12-3 and P12-4 were picked and inoculated into a 2 mL centrifuge tube with 1 mL of the YPD medium (containing 100 mg/L hygromycin B) in Example 1, incubated in a shaker at 250 RPM and 30° C. for 1 day. The above bacterial solution was taken into a 500 mL shake flask containing 30 mL of the seed medium of Example 1, wherein the inoculation amount was 3%, and incubated at 250 RPM and 30° C. until the $OD_{620}$ reached 0.8 (after 30-fold dilution). The seed solution was inoculated into a 500 mL shake flask containing 15 mL of the fermentation medium described in Example 1, in an amount of 20%, and the substrate in the fermentation medium was n-dodecane, and continued to culture at 250 RPM, 30° C. until the end of the fermentation. The original strain CCTCC M2011192 was used as control: the medium, culture and fermentation methods were the same as above, except that the YPD medium did not contain hygromycin B.

After the fermentation, the samples of 0.5 g of the fermentation broths were subjected to GC detection according to the method described in Step 4 of Example 1, and the yield of C12 dibasic acid and the mass ratio of monobasic acid impurity having 12 carbon atoms to C12 dibasic acid were calculated. The results were shown in Table 5 below.

TABLE 5

| Strain | Mass ratio of monobasic acid having 12 carbon atoms (%) | Yield of C12 dibasic acid (mg/g) |
|---|---|---|
| CCTCC231192 | 2.20 | 148.7 |
| 430HYG | 1.14 | 149.5 |
| P12-1 | 1.96 | 148.5 |
| P12-2 | 1.32 | 149.1 |
| P12-3 | 1.20 | 148.9 |
| P12-4 | 1.21 | 149.6 |

From the data of the content of monobasic acid impurity in Table 5, it can be inferred that the mutation site which significantly reduced the content of the monobasic acid impurity having 12 carbon atoms in the fermentation broth includes −579A>G, −412_−411AC>TT, −402insTT and −7_−4delACCA. Changes in these sites may affect the binding of a transcription factor to the cis-acting element of the promoter region, thereby affecting the transcription of the CYP52A gene.

Example 11 Fermentation of Strain 430 to Produce Long-Chain C10 Dibasic Acid

Fermentation: Strain 430 was inoculated to a 2 mL centrifuge tube containing 1 mL of YPD medium of Example 1, incubated at 30° C. on a shaker at 250 RPM for 1 day. The above bacterial solution was inoculated into a 500-mL shake flask with 30 mL of the seed medium of Example 1, wherein the inoculation amount was 3%, and cultured at 250 RPM and 30° C. for 36-48h until $OD_{620}$ reached 0.8 (after 30-fold dilution). The seed solution was inoculated into a shake flask containing 15 mL of the fermentation medium of Example 1, wherein the inoculation amount was 20%, and the substrate was n-decane in the fermentation medium. The culture on a shaker at 250 RPM and 30° C. was continued until the end of the fermentation. The strain CCTCC M2011192 was used as control, and the medium, culture and fermentation methods were the same as described above.

After fermentation, 0.5 g sample of the fermentation broth was taken and subjected to GC detection according to the method as described in Example 1 (4). The yield of C10 dibasic acid and the content of monobasic acid impurity of mutant strain were compared with the parental strain, and the results were shown in Table 6 below.

TABLE 6

| Strain | CCTCC M2011192 | 430 |
|---|---|---|
| Yield of C10 dibasic acid (mg/g) | 122.5 | 125.6 |
| Mass ratio of monobasic acid impurity having 10 carbon atoms (%) | 1.55 | 0.79 |

It can be seen from Table 6 that the mass ratio of monobasic acid impurity having 10 carbon atoms was decreased by 49.0%.

Extraction and purification steps: they were the same as the extraction and purification steps of Example 8, except for the absence of step (5). The purity of the primary and secondary C10 dibasic acid product and the content of monobasic acid impurity were determined and calculated using the method described in Example 1 (4), as shown in Table 7 below:

TABLE 7

| C10 dibasic acid | Strain | CCTCC M2011192 | 430 |
|---|---|---|---|
| Primary product | Purity of C10 dibasic acid (%) | 98.18 | 99.07 |
| | Content of monobasic acid impurity having 10 carbon atoms (ppm) | 3750 | 1835 |
| Secondary product | Purity of C10 dibasic acid (%) | 98.90 | 99.85 |
| | Content of monobasic acid impurity having 10 carbon atoms (ppm) | 535 | 280 |

Example 12 Production of Long-Chain C16 Dibasic Acid by Fermentation of the Strain 430

Fermentation: Strain 430 was inoculated to a 2 mL centrifuge tube containing 1 mL of YPD medium of Example 1, and incubated at 30° C. on a shaker at 250 RPM for 1 day. The above bacterial solution was inoculated into a 500-mL shake flask with 30 mL of the seed medium of Example 1, wherein the inoculation amount was 3%, and cultured at 250 RPM and 30° C. for 36-48h until $OD_{620}$ reached 0.8 (after 30-fold dilution). The seed solution was inoculated into a shake flask containing 15 mL of the fermentation medium of Example 1, wherein the inoculation amount was 20%, and the substrate was n-hexadecane in the fermentation medium. The culture on a shaker at 250 RPM and 30° C. was continued until the end of the fermentation. The strain CCTCC M2011192 was used as control, and the medium, culture and fermentation methods were the same as described above.

After the fermentation, 0.5 g sample of the fermentation broth was taken and subjected to GC detection according to the method described in Example 1 (4). The yield of C16 dibasic acid and the content of monobasic acid impurity of mutant strain were compared with the parental strain, and the results were shown in Table 8 below.

TABLE 8

| Strain | CCTCC M2011192 | 430 |
|---|---|---|
| Yield of C16 dibasic acid (mg/g) | 125.1 | 126.6 |
| Mass ratio of monobasic acid impurity having 16 carbon atoms (%) | 5.06 | 2.89 |

It can be seen from Table 8 that the mass ratio of monobasic acid impurity having 16 carbon atoms was decreased by 42.9%.

Extraction and purification steps were the same as the extraction and purification steps of Example 8, except for the absence of step (5). The purity of the primary and secondary C16 dibasic acid product as well as the content of monobasic acid impurity were determined and calculated using the method described in Example 1 (4), as shown in Table 9 below:

TABLE 9

| C16 dibasic acid | Strain | CCTCC M2011192 | 430 |
|---|---|---|---|
| Primary product | Purity of C16 dibasic acid (%) | 81.10 | 83.50 |
| | Content of monobasic acid impurity having 16 carbon atoms (ppm) | 13650 | 10240 |
| Secondary product | Purity of C16 dibasic acid (%) | 98.40 | 99.15 |
| | Content of monobasic acid impurity having 16 carbon atoms (ppm) | 6205 | 3470 |

Example 13

The DNA fragment (SEQ ID NO: 13) in Example 9 was introduced into *Candida tropicalis* (CCTCC M 203052) by homologous recombination according to the methods as described in Examples 4 and 5. The method for sequencing the promoter of the gene CYP52A12 of the obtained single colony and the parent strain (CCTCC M 203052) were the same as described in Example 6. By sequencing, it was confirmed that the sequence of the gene CYP52A12 in the parent strain (CCTCC M 203052) was consistent with the published sequence in GenBank with the Accession Number of AY230498, while the screened out colony carried a mutation in this gene in which the mutation was consistent with SEQ ID NO: 16. One strain was designated as 432HYG.

The method for fermentation was according to Example 5, in which the strains used were CCTCC M 203052 and 432HYG. After completion of fermentation, a sample of 0.5 g of each fermentation broth was collected, and the yield of C12 dibasic acid and the amount of monobasic acid impurity having 12 carbon atoms were calculated, as shown in Table 10. The results indicated that the content of the monobasic acid impurity in the fermentation broth by the strain 432HYG was significantly reduced compared with the parent strain CCTCC M 203052.

TABLE 10

| Strain | CCTCC M203052 | 432HYG |
|---|---|---|
| Yield of C12 dibasic acid (mg/g) | 135.8 | 134.1 |
| Mass ratio of monobasic acid impurity having 12 carbon atoms (%) | 1.23 | 0.59 |

From the above Examples 8-13 regarding the fermentation production of long-chain dibasic acids from different fermentation substrates, it can be seen that the content of monobasic acid impurity in the fermentation broth after fermentation was significantly reduced; compared to the parental strain, the content of monobasic acid impurity could be reduced by more than 40%, and sometimes reduced by nearly 50%, and further extraction and purification of the obtained C12, C10 and C16 dibasic acids could further reduce the content of monobasic acid impurity, which reduces the difficulty of the later extraction and purification processes to a great extent.

The invention claimed is:

1. A product, which is one of the products I) and II):

I) an isolated DNA molecule, which, corresponding to nucleotides 1-1176 or 265-1176 of SEQ ID NO: 21, wherein SEQ ID NO: 21 comprises a gene encoding a CYP52A12 protein, comprises any one or more of base mutations 301A>G, 324A>T, 346delT, 352C>A, 354delG, 598A>G, 765_766AC>TT, 774insTT and 1162_1176ACCAACCAACCAACC (SEQ ID NO: 39)>ACCAACCAACC (SEQ ID NO: 40), wherein the promoter region, the isolated DNA molecule has at least 95% sequence identity to SEQ ID NO: 16; and II) a microorganism containing the isolated DNA molecule of I), which produces a long-chain dibasic acid with decreased content of monobasic acid impurity, compared to a microorganism not containing the isolated DNA molecule of I), wherein the decreased content of monobasic acid impurity is more than 0, and less than 12,000 parts per million (ppm), 10,000 ppm, 6,000 ppm, 3,000 ppm, 1,000 ppm, 500 ppm, or 200 ppm or less.

2. The product of claim 1, which is I) the isolated DNA molecule, wherein the isolated DNA molecule comprises:

(ii) base mutations 765_766AC>TT, 774insTT and 1162_1176ACCAACCAACCAACC (SEQ ID NO: 39)>ACCAACCAACC (SEQ ID NO: 40); or (vi) a sequence comprising the nucleotide sequence set forth in any of SEQ ID NOs: 27-36.

3. The product of claim 1, which is II) the microorganism, wherein the microorganism is:

(i) selected from the group consisting of *Corynebacterium, Geotrichum candidum, Candida, Pichia, Rhodotroula, Saccharomyces* and *Yarrowia;*

(ii) yeast; or (iii) *Candida tropicalis* or *Candida sake.*

4. The product of claim 1, which is II) the microorganism, wherein the long-chain dibasic acid is:

(i) selected from the group consisting of C9 to C22 long-chain dibasic acids;

(ii) selected from the group consisting of C9 to C18 long-chain dibasic acids;

(iii) one or more selected from the group consisting of C10 dibasic acid, C11 dibasic acid, C12 dibasic acid, C13 dibasic acid, C14 dibasic acid, C15 dibasic acid and C16 dibasic acid;

(iv) at least one or more of C10 to C16 dibasic acids, or at least one or more of n-C10 to C16 dibasic acids; or (v) at least one or more selected from the group consisting of sebacic acid, undecanedioic acid, dodecanedioic acid, tridecanedioic acid, tetradecanedioic acid, pentadecanedioic acid and hexadecanedioic acid.

5. The product of claim 1, which is II) the microorganism, wherein the monobasic acid impurity:

(i) comprises those having the chemical formula of $CH_3$—$(CH_2)$n-COOH, where n≥7, and/or $CH_2OH$—$(CH_2)$n-COOH, where n≥7;

(ii) comprises, but not limited to, a long-chain monobasic acid with the number of carbon atoms in the carbon chain greater than 9; or (iii) comprises any one or more selected from the group consisting of a monobasic acid having 9 carbon atoms, a monobasic acid having 10 carbon atoms, a monobasic acid having 11 carbon atoms, a monobasic acid having 12 carbon atoms, a monobasic acid having 13 carbon atoms, a monobasic acid having 14 carbon atoms, a monobasic acid having 15 carbon atoms, a monobasic acid having 16 carbon atoms, a monobasic acid having 17 carbon atoms, a monobasic acid having 18 carbon atoms, and a monobasic acid having 19 carbon atoms.

6. A method of producing a long-chain dibasic acid or fermentation broth comprising long chain dibasic acid, comprising culturing the microorganism of claim 1 II), a microorganism containing the isolated DNA molecule of claim 1 I), which produces a long-chain dibasic acid with decreased content of monobasic acid impurity, compared to a microorganism not containing the isolated DNA molecule of claim 1 I), and in the method of producing a long chain dibasic acid, isolating, extracting and/or purifying the long-chain dibasic acid from the culture.

7. The method of claim 6, wherein the microorganism is:

(i) selected from the group consisting of *Corynebacterium, Geotrichum candidum, Candida, Pichia, Rhodotroula, Saccharomyces* and *Yarrowia;*

(ii) yeast; or (iii) *Candida tropicalis* or *Candida sake.*

8. The method of claim 6, wherein the long-chain dibasic acid is:

(i) selected from the group consisting of C9 to C22 long-chain dibasic acids;

(ii) selected from the group consisting of C9 to C18 long-chain dibasic acids;

(iii) one or more selected from the group consisting of C10 dibasic acid, C11 dibasic acid, C12 dibasic acid, C13 dibasic acid, C14 dibasic acid, C15 dibasic acid and C16 dibasic acid;

(iv) at least one or more of C10 to C16 dibasic acids, or at least one or more of n-C10 to C16 dibasic acids; or (v) at least one or more selected from the group consisting of sebacic acid, undecanedioic acid, dodecanedioic acid, tridecanedioic acid, tetradecanedioic acid, pentadecanedioic acid and hexadecanedioic acid.

9. The method of claim 6, wherein the monobasic acid impurity:

(i) comprises those having a chemical formula of $CH_3$—$(CH_2)$n-COOH, where n≥7, and/or $CH_2OH$—$(CH_2)$n-COOH, where n≥7;

(ii) comprises, a long-chain monobasic acid with a number of carbon atoms in a carbon chain greater than 9;

(iii) comprises any one or more selected from the group consisting of a monobasic acid having 9 carbon atoms, a monobasic acid having 10 carbon atoms, a monobasic acid having 11 carbon atoms, a monobasic acid having 12 carbon atoms, a monobasic acid having 13 carbon atoms, a monobasic acid having 14 carbon atoms, a monobasic acid having 15 carbon atoms, a monobasic acid having 16 carbon atoms, a monobasic acid having 17 carbon atoms, a monobasic acid having 18 carbon atoms, and a monobasic acid having 19 carbon atoms; or (iv) is decreased in content by at least 5%, at least 10%, at least 20%, at least 40%, at least 50% or more, compared to that in the long-chain dibasic acid produced by fermentation with a microorganism not containing the isolated DNA molecule of claim 1 I).

* * * * *

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: primer Pcyp52a12-F

<400> SEQUENCE: 1

gtcgacttct cctttaggca                                      20


<210> SEQ ID NO 2
<211> LENGTH: 20
<212> TYPE: DNA
<213> ORGANISM: Artificial Sequence
```

<220> FEATURE:
<223> OTHER INFORMATION: primer Pcyp52a12-R

<400> SEQUENCE: 2
tcgatgattt cttgtgtggc 20

<210> SEQ ID NO 3
<211> LENGTH: 21
<212> TYPE: DNA
<213> ORGANISM: Artificial Sequence
<220> FEATURE:
<223> OTHER INFORMATION: primer CYP52A12_Upstream-F

<400> SEQUENCE: 3
ggtcgaggaa gtggcattaa a 21

<210> SEQ ID NO 4
<211> LENGTH: 18
<212> TYPE: DNA
<213> ORGANISM: Artificial Sequence
<220> FEATURE:
<223> OTHER INFORMATION: primer CYP52A12_Upstream-R

<400> SEQUENCE: 4
acctcctgca gttgccat 18

<210> SEQ ID NO 5
<211> LENGTH: 20
<212> TYPE: DNA
<213> ORGANISM: Artificial Sequence
<220> FEATURE:
<223> OTHER INFORMATION: primer CYP52A12_Downstream-F

<400> SEQUENCE: 5
atggccacac aagaaatcat 20

<210> SEQ ID NO 6
<211> LENGTH: 20
<212> TYPE: DNA
<213> ORGANISM: Artificial Sequence
<220> FEATURE:
<223> OTHER INFORMATION: primer CYP52A12_Downstream-R

<400> SEQUENCE: 6
agtctgggag taacttctgg 20

<210> SEQ ID NO 7
<211> LENGTH: 38
<212> TYPE: DNA
<213> ORGANISM: Artificial Sequence
<220> FEATURE:
<223> OTHER INFORMATION: primer CYP52A12_HYG-F

<400> SEQUENCE: 7
atggcaactg caggaggtgc atgcgaaccc gaaaatgg 38

<210> SEQ ID NO 8
<211> LENGTH: 40
<212> TYPE: DNA
<213> ORGANISM: Artificial Sequence
<220> FEATURE:
<223> OTHER INFORMATION: primer CYP52A12_HYG-R

<400> SEQUENCE: 8
tgcctaaagg agaagtcgac gctagcagct ggatttcact 40

<210> SEQ ID NO 9
<211> LENGTH: 1776
<212> TYPE: DNA
<213> ORGANISM: Artificial Sequence
<220> FEATURE:
<223> OTHER INFORMATION: HYG

<400> SEQUENCE: 9
atggcaactg caggaggtgc atgcgaaccc gaaaatggag caatcttccc cggggcctcc 60
aaataccaac tcacccgaga gagataaaga gacaccaccc accacgagac ggagtatatc 120
caccaaggta agtaactcag agttaatgat acaggtgtac acagctcctt ccctagccat 180
tgagtgggta tcacatgaca ctggtaggtt acaaccacgt ttagtagtta ttttgtgcaa 240
ttccatgggg atcaggaagt ttggtttggt gggtgcgtct actgattccc ctttgtctct 300
gaaaatcttt tccctagtgg aacactttgg ctgaatgata taaattcacc ttgattccca 360
ccctcccttc tttctctctc tctctgttac acccaattga attttctttt tttttttact 420
ttccctcctt ctttatcatc aaagataagt aagtttatca attgcctatt cagaatgaaa 480
aagcctgaac tcaccgcgac gtctgtcgag aagtttctca tcgaaaagtt cgacagcgtc 540
tccgacctca tgcagctctc ggagggcgaa gaatctcgtg ctttcagctt cgatgtagga 600
gggcgtggat atgtcctccg ggtaaatagc tgcgccgatg gtttctacaa agatcgttat 660
gtttatcggc actttgcatc ggccgcgctc ccgattccgg aagtgcttga cattggggaa 720
ttcagcgaga gcctcaccta ttgcatctcc cgccgtgcac agggtgtcac gttgcaagac 780
ctccctgaaa ccgaactccc cgctgttctc cagccggtcg cggaggccat ggatgcgatc 840
gctgcggccg atcttagcca gacgagcggg ttcggcccat tcggaccgca aggaatcggt 900
caatacacta catggcgtga tttcatatgc gcgattgctg atccccatgt gtatcactgg 960
caaactgtga tggacgacac cgtcagtgcg tccgtcgcgc aggctctcga tgagctcatg 1020
ctttgggccg aggactgccc cgaagtccgg cacctcgtgc acgcggattt cggctccaac 1080
aatgtcctca cggacaatgg ccgcataaca gcggtcattg actggagcga ggcgatgttc 1140
ggggattccc aatacgaggt cgccaacatc ttcttctgga ggccgtggtt ggcttgtatg 1200
gagcagcaga cgcgctactt cgagcggagg catccggagc ttgcaggatc gccgcggctc 1260
cgggcgtata tgctccgcat tggtcttgac caactctatc agagcttggt tgacggcaat 1320
ttcgatgatg cagcttgggc gcagggtcga tgcgacgcaa tcgtccgatc cggagccggg 1380
actgtcgggc gtacacaaat cgcccgcaga agcgcggccg tctggaccga tggctgtgta 1440
gaagtactcg ccgatagtgg aaaccgacgc cccagcactc gtccgagggc aaaggaatag 1500
tgtgctaccc acgcttactc caccagagct attaacatca gaaatattta ttctaataaa 1560
taggatgcaa aaaaaaaacc cccttaata aaaaaaaaag aaacgatttt ttatctaatg 1620
aagtctatgt atctaacaaa tgtatgtatc aatgtttatt ccgttaaaca aaaatcagtc 1680
tgtaaaaaag gttctaaata aatattctgt ctagtgtaca cattctccca aaatagtgaa 1740
atccagctgc tagcttgtcg acttctcctt taggca 1776

<210> SEQ ID NO 10
<211> LENGTH: 38
<212> TYPE: DNA
<213> ORGANISM: Artificial Sequence
<220> FEATURE:
<223> OTHER INFORMATION: primer CYP52A12_Upstream-2R

<400> SEQUENCE: 10

-continued tgcctaaagg agaagtcgac acctcctgca gttgccat 38

<210> SEQ ID NO 11
<211> LENGTH: 5873
<212> TYPE: DNA
<213> ORGANISM: Artificial Sequence
<220> FEATURE:
<223> OTHER INFORMATION: vector pCIB2

<400> SEQUENCE: 11
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcggtct 240
agtatgattg tcaataatga tgggtcatcg tttcctgatt cgacgttccc tgtggtgtcg 300
ttaaatagcc tgtctgaaat ctcctccatg attgtgttgg tgtgtgttgt ttgactttcc 360
caattgctta cattttttc ttcaaggatt cgctccaaaa tagacagaaa ttatcgcgac 420
aagtcagacg aacgtcgcac gaggcgaacc aaattcttta gaagcatacg aaaactcact 480
ttatttccat tagaagtatt aaattaacaa atatataata tacaggatac aaagtaaaag 540
cacgcttaag caaccaaagc ggaagcggta gcggattcgt atttccagtt aggtggcaag 600
acagcgacgg ttctgtagta tctggccaat ctgtggattc tagattcaat caaaatcaat 660
ctgaacttgg agtccttgtc ctttctgttt ctttccaagt gctttctgac agagacagcc 720
ttcttgatca agtagtacaa gtcttctggg atttctggag ccaaaccgtt ggatttcaag 780
attctcaaga tcttgttacc agtgacaacc ttggcttggg aaacaccgtg agcatctctc 840
aagataacac caatttgaga tggagtcaaa ccctttctgg cgtacttgat gacttgttca 900
acaacttcgt cagaagacaa cttgaaccaa gatggagcgt ttcttgagta tggaagagcg 960
gaggaggaaa tacctttacc ctaaaataac aagagctaat gttagtaatt tgaaaaaaaa 1020
gacgttgagc acgcacaccc catccacccc acaggtgaaa cacatcaaac gtagcaagaa 1080
caatagttgg ccctcccgtc aagggggcag gtaattgtcc aagtacttta gaaaagtatg 1140
tttttaccca taagatgaac acacacaaac cagcaaaagt atcaccttct gcttttcttg 1200
gttgaggttc aaattatgtt tggcaataat gcagcgacaa tttcaagtac ctaaagcgta 1260
tatagtaaca attctaggtc tgtatagtcg accgtaggtg aatcgtttac tttaggcaag 1320
accttgtccc tgataaagcc aggttgtact ttctattcat tgagtgtcgt ggtggtggta 1380
gtggtggttg attgggctgt tgtggtagta gtagtggttg tgatttggaa catacagatg 1440
aatgcatacg acccatgatg actgatttgt ttctttattg agttgatggt aagaaagaga 1500
agaagaggag gtaaaaaggt ggtagagtga aaaatttttt tctcttaaaa gtgagagaga 1560
gaaagagaaa aatttcactg cgaaacaaat ggttggggac acgacttttt tcaggaattt 1620
ttactcgaag cgtatatgca ggaaagttgt tgttagggaa tatggagcca caagagagct 1680
gcgaattcga gctcggtacc cggggatcct ctagagtcga cctgcaggca tgcgaacccg 1740
aaaatggagc aatcttcccc ggggcctcca aataccaact cacccgagag agagaaagag 1800
acaccaccca ccacgagacg gagtatatcc accaaggtaa gtaactcagg gttaatgata 1860
caggtgtaca cagctccttc cctagccatt gagtgggtat cacatgacac tggtaggtta 1920
caaccacgtt tagtagttat tttgtgcaat tccatgggga tcaggaagtt tggtttggtg 1980

-continued

```
ggtgcgtcta ctgattcccc tttgtctctg aaaatctttt ccctagtgga acactttggc   2040
tgaatgatat aaattcacct tgattcccac cctcccttct ttctctctct ctctgttaca   2100
cccaattgaa ttttcttttt ttttttactt tccctccttc tttatcatca aagataagta   2160
agtttatcaa ttgcctattc agaatgaaaa agcctgaact caccgcgacg tctgtcgaga   2220
agtttctcat cgaaaagttc gacagcgtct ccgacctcat gcagctctcg gagggcgaag   2280
aatctcgtgc tttcagcttc gatgtaggag ggcgtggata tgtcctccgg gtaaatagct   2340
gcgccgatgg tttctacaaa gatcgttatg tttatcggca ctttgcatcg gccgcgctcc   2400
cgattccgga agtgcttgac attggggaat tcagcgagag cctcacctat tgcatctccc   2460
gccgtgcaca gggtgtcacg ttgcaagacc tccctgaaac cgaactcccc gctgttctcc   2520
agccggtcgc ggaggccatg gatgcgatcg ctgcggccga tcttagccag acgagcgggt   2580
tcggcccatt cggaccgcaa ggaatcggtc aatacactac atggcgtgat ttcatatgcg   2640
cgattgctga tccccatgtg tatcactggc aaactgtgat ggacgacacc gtcagtgcgt   2700
ccgtcgcgca ggctctcgat gagctcatgc tttgggccga ggactgcccc gaagtccggc   2760
acctcgtgca cgcggatttc ggctccaaca atgtcctcac ggacaatggc cgcataacag   2820
cggtcattga ctggagcgag gcgatgttcg gggattccca atacgaggtc gccaacatct   2880
tcttctggag gccgtggttg gcttgtatgg agcagcagac gcgctacttc gagcggaggc   2940
atccggagct tgcaggatcg ccgcggctcc gggcgtatat gctccgcatt ggtcttgacc   3000
aactctatca gagcttggtt gacggcaatt tcgatgatgc agcttgggcg cagggtcgat   3060
gcgacgcaat cgtccgatcc ggagccggga ctgtcgggcg tacacaaatc gcccgcagaa   3120
gcgcggccgt ctggaccgat ggctgtgtag aagtactcgc cgatagtgga aaccgacgcc   3180
ccagcactcg tccgagggca aaggaatagt gtgctaccca cgcttactcc accagagcta   3240
ttaacatcag aaatatttat tctaataaat aggatgcaaa aaaaaaaccc cccttaataa   3300
aaaaaaaaga aacgattttt tatctaatga agtctatgta tctaacaaat gtatgtatca   3360
atgtttattc cgttaaacaa aaatcagtct gtaaaaaagg ttctaaataa atattctgtc   3420
tagtgtacac attctcccaa aatagtgaaa tccagctgct agcgtgtaag cttggcactg   3480
gccgtcgttt tacaacgtcg tgactgggaa aaccctggcg ttacccaact taatcgcctt   3540
gcagcacatc cccctttcgc cagctggcgt aatagcgaag aggcccgcac cgatcgccct   3600
tcccaacagt tgcgcagcct gaatggcgaa tggcgcctga tgcggtattt tctccttacg   3660
catctgtgcg gtatttcaca ccgcatatgg tgcactctca gtacaatctg ctctgatgcc   3720
gcatagttaa gccagccccg acacccgcca acacccgctg acgcgccctg acgggcttgt   3780
ctgctcccgg catccgctta cagacaagct gtgaccgtct ccgggagctg catgtgtcag   3840
aggttttcac cgtcatcacc gaaacgcgcg agacgaaagg gcctcgtgat acgcctattt   3900
ttataggtta atgtcatgat aataatggtt tcttagacgt caggtggcac ttttcgggga   3960
aatgtgcgcg gaacccctat ttgtttattt ttctaaatac attcaaatat gtatccgctc   4020
atgagacaat aaccctgata aatgcttcaa taatattgaa aaaggaagag tatgagtatt   4080
caacatttcc gtgtcgccct tattcccttt tttgcggcat tttgccttcc tgtttttgct   4140
cacccagaaa cgctggtgaa agtaaaagat gctgaagatc agttgggtgc acgagtgggt   4200
tacatcgaac tggatctcaa cagcggtaag atccttgaga gttttcgccc cgaagaacgt   4260
tttccaatga tgagcacttt taaagttctg ctatgtggcg cggtattatc ccgtattgac   4320
gccgggcaag agcaactcgg tcgccgcata cactattctc agaatgactt ggttgagtac   4380
```

```
tcaccagtca cagaaaagca tcttacggat ggcatgacag taagagaatt atgcagtgct   4440

gccataacca tgagtgataa cactgcggcc aacttacttc tgacaacgat cggaggaccg   4500

aaggagctaa ccgctttttt gcacaacatg ggggatcatg taactcgcct tgatcgttgg   4560

gaaccggagc tgaatgaagc cataccaaac gacgagcgtg acaccacgat gcctgtagca   4620

atggcaacaa cgttgcgcaa actattaact ggcgaactac ttactctagc ttcccggcaa   4680

caattaatag actggatgga ggcggataaa gttgcaggac cacttctgcg ctcggccctt   4740

ccggctggct ggtttattgc tgataaatct ggagccggtg agcgtgggtc tcgcggtatc   4800

attgcagcac tggggccaga tggtaagccc tcccgtatcg tagttatcta cacgacgggg   4860

agtcaggcaa ctatggatga acgaaataga cagatcgctg agataggtgc ctcactgatt   4920

aagcattggt aactgtcaga ccaagtttac tcatatatac tttagattga tttaaaactt   4980

catttttaat ttaaaaggat ctaggtgaag atcctttttg ataatctcat gaccaaaatc   5040

ccttaacgtg agttttcgtt ccactgagcg tcagaccccg tagaaaagat caaaggatct   5100

tcttgagatc ctttttttct gcgcgtaatc tgctgcttgc aaacaaaaaa accaccgcta   5160

ccagcggtgg tttgtttgcc ggatcaagag ctaccaactc tttttccgaa ggtaactggc   5220

ttcagcagag cgcagatacc aaatactgtc cttctagtgt agccgtagtt aggccaccac   5280

ttcaagaact ctgtagcacc gcctacatac ctcgctctgc taatcctgtt accagtggct   5340

gctgccagtg gcgataagtc gtgtcttacc gggttggact caagacgata gttaccggat   5400

aaggcgcagc ggtcgggctg aacggggggt tcgtgcacac agcccagctt ggagcgaacg   5460

acctacaccg aactgagata cctacagcgt gagctatgag aaagcgccac gcttcccgaa   5520

gggagaaagg cggacaggta tccggtaagc ggcagggtcg gaacaggaga gcgcacgagg   5580

gagcttccag ggggaaacgc ctggtatctt tatagtcctg tcgggtttcg ccacctctga   5640

cttgagcgtc gatttttgtg atgctcgtca ggggggcgga gcctatggaa aaacgccagc   5700

aacgcggcct ttttacggtt cctggccttt tgctggcctt ttgctcacat gttctttcct   5760

gcgttatccc ctgattctgt ggataaccgt attaccgcct ttgagtgagc tgataccgct   5820

cgccgcagcc gaacgaccga gcgcagcgag tcagtgagcg aggaagcgga aga          5873
```

<210> SEQ ID NO 12
<211> LENGTH: 1424
<212> TYPE: DNA
<213> ORGANISM: Artificial Sequence
<220> FEATURE:
<223> OTHER INFORMATION: homologous recombination template

<400> SEQUENCE: 12

```
ggtcgaggaa gtggcattaa atccatgcga tgatcgcagg agatcagaat caaattgttg     60

ggttctagcg taacttcgtt aattacatga ggagtggagt aagcgtaata tgcgcgaagg    120

gctcagaacc gcacgtgact tcccctaaca ttgtagttaa gaggggaggg atcggagttt    180

ctttttggt tgtgcacgga gaaatcgttg aaaaggtggg gcacattttc atatgcgcta    240

atcttctttt tctttttatc acaggagaaa ctatcccacc cccacttcga aacacaatga    300

caactcctgc gtaacttgca aattcttgtc tgactaattg aaaactccgg acgagtcaga    360

cctccagtca aacggacaga cagacaaaca cttggtgcga tgttcatacc tacagacatg    420

tcaacgggtg ttagacgacg gtttcttgca aagacaggtg ttggcatctc gtacgatggc    480

aactgcagga ggtgtcgact tctcctttag gcaatagaaa aagactaagg gaacagcgtt    540
```

-continued

```
tttacaggtt gctttggtta atgtagtatt ttttagtcca acattctgtg ggttgctctg    600

ggtttctaga ataggaaatc acaggagaat gcaaattcag atggaagaac aaagagataa    660

aaaacaaaaa aaaactgagt tttgcaccaa tagaatgttt gatgatatca tccactcgct    720

aaacgaatca tgtgggtgat cttctcttta gttttggtct atcataaaac acatgaaagt    780

gaaatccaaa tacactacac tccgggtatt gtccttcgtt ttacggatgt ctcattgtct    840

tacttttgag gtcataggag ttgcctgtga gagatcacag agattatcac actcacattt    900

atcgtagttt cctatctcat gctgtgtgtc tctggttggt tcatgagttt ggattgttgt    960

acattaaagg aatcgctgga aagcaaagct atttaaattt tttctttgtc acaggtacac   1020

taacctgtaa aacttcactg ccacgccagt ctttcctgat tgggcaagtg cacaaactac   1080

aacctgcaaa acagcactcc gcttgtcaca ggttgtctcc tctcaaccaa caaaaaaata   1140

agattaaact ttctttgctc atgcatcaat cggagttatc tctgaaagag ttgcctttgt   1200

gtaatgtgtg ccaaactcaa actgcaaaac taaccacaga atgatttccc tcacaattat   1260

ataaactcac ccacatttcc acagaccgta atttcatgtc tcactttctc ttttgctctt   1320

cttttactta gtcaggtttg ataacttcct tttttattac cctatcttat ttatttattt   1380

attcatttat accaaccaac catggccaca caagaaatca tcga                    1424
```

<210> SEQ ID NO 13
<211> LENGTH: 3162
<212> TYPE: DNA
<213> ORGANISM: Artificial Sequence
<220> FEATURE:
<223> OTHER INFORMATION: DNA fragment comprising mutant CYP52A12 and the resistance gene HYG

<400> SEQUENCE: 13

```
ggtcgaggaa gtggcattaa atccatgcga tgatcgcagg agatcagaat caaattgttg     60

ggttctagcg taacttcgtt aattacatga ggagtggagt aagcgtaata tgcgcgaagg    120

gctcagaacc gcacgtgact tcccctaaca ttgtagttaa gaggggaggg atcggagttt    180

ctttttggt tgtgcacgga gaaatcgttg aaaaggtggg gcacattttc atatgcgcta    240

atcttctttt tctttttatc acaggagaaa ctatcccacc cccacttcga aacacaatga    300

caactcctgc gtaacttgca aattcttgtc tgactaattg aaaactccgg acgagtcaga    360

cctccagtca aacggacaga cagacaaaca cttggtgcga tgttcatacc tacagacatg    420

tcaacgggtg ttagacgacg gtttcttgca aagacaggtg ttggcatctc gtacgatggc    480

aactgcagga ggtgcatgcg aacccgaaaa tggagcaatc ttccccgggg cctccaaata    540

ccaactcacc cgagagagat aaagagacac cacccaccac gagacggagt atatccacca    600

aggtaagtaa ctcagagtta atgatacagg tgtacacagc tccttcccta gccattgagt    660

gggtatcaca tgacactggt aggttacaac cacgtttagt agttattttg tgcaattcca    720

tggggatcag gaagtttggt ttggtgggtg cgtctactga ttccccttg tctctgaaaa    780

tcttttccct agtggaacac tttggctgaa tgatataaat tcaccttgat tcccaccctc    840

ccttctttct ctctctctct gttacaccca attgaatttt cttttttttt ttactttccc    900

tccttcttta tcatcaaaga taagtaagtt tatcaattgc ctattcagaa tgaaaaagcc    960

tgaactcacc gcgacgtctg tcgagaagtt tctcatcgaa aagttcgaca gcgtctccga   1020

cctcatgcag ctctcggagg gcgaagaatc tcgtgctttc agcttcgatg taggagggcg   1080

tggatatgtc ctccgggtaa atagctgcgc cgatggtttc tacaaagatc gttatgttta   1140
```

-continued

```
tcggcacttt gcatcggccg cgctcccgat tccggaagtg cttgacattg gggaattcag   1200
cgagagcctc acctattgca tctcccgccg tgcacagggt gtcacgttgc aagacctccc   1260
tgaaaccgaa ctccccgctg ttctccagcc ggtcgcggag gccatggatg cgatcgctgc   1320
ggccgatctt agccagacga gcgggttcgg cccattcgga ccgcaaggaa tcggtcaata   1380
cactacatgg cgtgatttca tatgcgcgat tgctgatccc catgtgtatc actggcaaac   1440
tgtgatggac gacaccgtca gtgcgtccgt cgcgcaggct ctcgatgagc tcatgctttg   1500
ggccgaggac tgccccgaag tccggcacct cgtgcacgcg gatttcggct ccaacaatgt   1560
cctcacggac aatggccgca taacagcggt cattgactgg agcgaggcga tgttcgggga   1620
ttcccaatac gaggtcgcca acatcttctt ctggaggccg tggttggctt gtatggagca   1680
gcagacgcgc tacttcgagc ggaggcatcc ggagcttgca ggatcgccgc ggctccgggc   1740
gtatatgctc cgcattggtc ttgaccaact ctatcagagc ttggttgacg gcaatttcga   1800
tgatgcagct tgggcgcagg gtcgatgcga cgcaatcgtc cgatccggag ccgggactgt   1860
cgggcgtaca caaatcgccc gcagaagcgc ggccgtctgg accgatggct gtgtagaagt   1920
actcgccgat agtggaaacc gacgccccag cactcgtccg agggcaaagg aatagtgtgc   1980
tacccacgct tactccacca gagctattaa catcagaaat atttattcta ataaatagga   2040
tgcaaaaaaa aaaccccccct taataaaaaa aaaagaaacg attttttatc taatgaagtc   2100
tatgtatcta acaaatgtat gtatcaatgt ttattccgtt aaacaaaaat cagtctgtaa   2160
aaaaggttct aaataaatat tctgtctagt gtacacattc tcccaaaata gtgaaatcca   2220
gctgctagct tgtcgacttc tcctttaggc aatagaaaaa gactaaggga acagcgtttt   2280
tacaggttgc tttggttaat gtagtatttt ttagtccaac attctgtggg ttgctctggg   2340
tttctagaat aggaaatcac aggagaatgc aaattcagat ggaagaacaa agagataaaa   2400
aacaaaaaaa aactgagttt tgcaccaata gaatgtttga tgatatcatc cactcgctaa   2460
acgaatcatg tgggtgatct tctctttagt tttggtctat cataaaacac atgaaagtga   2520
aatccaaata cactacactc cgggtattgt ccttcgtttt acggatgtct cattgtctta   2580
cttttgaggt cataggagtt gcctgtgaga gatcacagag attatcacac tcacatttat   2640
cgtagtttcc tatctcatgc tgtgtgtctc tggttggttc atgagtttgg attgttgtac   2700
attaaaggaa tcgctggaaa gcaaagctat ttaaattttt tctttgtcac aggtacacta   2760
acctgtaaaa cttcactgcc acgccagtct ttcctgattg ggcaagtgca caaactacaa   2820
cctgcaaaac agcactccgc ttgtcacagg ttgtctcctc tcaaccaaca aaaaaataag   2880
attaaacttt ctttgctcat gcatcaatcg gagttatctc tgaaagagtt gcctttgtgt   2940
aatgtgtgcc aaactcaaac tgcaaaacta accacagaat gatttccctc acaattatat   3000
aaactcaccc acatttccac agaccgtaat ttcatgtctc actttctctt ttgctcttct   3060
tttacttagt caggtttgat aacttccttt tttattaccc tatcttattt atttatttat   3120
tcatttatac caaccaacca tggccacaca agaaatcatc ga                      3162
```

<210> SEQ ID NO 14
<211> LENGTH: 513
<212> TYPE: DNA
<213> ORGANISM: Artificial Sequence
<220> FEATURE:
<223> OTHER INFORMATION: recombination template fragment CYP52A-
Upstream-2

<400> SEQUENCE: 14
ggtcgaggaa gtggcattaa atccatgcga tgatcgcagg agatcagaat caaattgttg 60
ggttctagcg taacttcgtt aattacatga ggagtggagt aagcgtaata tgcgcgaagg 120
gctcagaacc gcacgtgact tcccctaaca ttgtagttaa gaggggaggg atcggagttt 180 ctttttggt tgtgcacgga gaaatcgttg aaaaggtggg gcacattttc atatgcgcta 240
atcttctttt tctttttatc acaggagaaa ctatcccacc cccacttcga aacacaatga 300
caactcctgc gtaacttgca aattcttgtc tgactaattg aaaactccgg acgagtcaga 360
cctccagtca aacggacaga cagacaaaca cttggtgcga tgttcatacc tacagacatg 420
tcaacgggtg ttagacgacg gtttcttgca aagacaggtg ttggcatctc gtacgatggc 480
aactgcagga ggtgtcgact tctcctttag gca 513

<210> SEQ ID NO 15
<211> LENGTH: 931
<212> TYPE: DNA
<213> ORGANISM: Artificial Sequence
<220> FEATURE:
<223> OTHER INFORMATION: recombination template fragment Pcyp52a12

<400> SEQUENCE: 15
gtcgacttct cctttaggca atagaaaaag actaagggaa cagcgttttt acaggttgct 60
ttggttaatg tagtattttt tagtccaaca ttctgtgggt tgctctgggt ttctagaata 120
ggaaatcaca ggagaatgca aattcagatg gaagaacaaa gagataaaaa acaaaaaaaa 180
actgagtttt gcaccaatag aatgtttgat gatatcatcc actcgctaaa cgaatcatgt 240
gggtgatctt ctctttagtt ttggtctatc ataaaacaca tgaaagtgaa atccaaatac 300
actacactcc gggtattgtc cttcgtttta cggatgtctc attgtcttac ttttgaggtc 360
ataggagttg cctgtgagag atcacagaga ttatcacact cacatttatc gtagtttcct 420
atctcatgct gtgtgtctct ggttggttca tgagtttgga ttgttgtaca ttaaaggaat 480
cgctggaaag caaagctatt taaatttttt ctttgtcaca ggtacactaa cctgtaaaac 540
ttcactgcca cgccagtctt tcctgattgg gcaagtgcac aaactacaac ctgcaaaaca 600
gcactccgct tgtcacaggt tgtctcctct caaccaacaa aaaaataaga ttaaactttc 660
tttgctcatg catcaatcgg agttatctct gaaagagttg cctttgtgta atgtgtgcca 720
aactcaaact gcaaaactaa ccacagaatg atttccctca caattatata aactcaccca 780
catttccaca gaccgtaatt tcatgtctca ctttctcttt tgctcttctt ttacttagtc 840
aggtttgata acttcctttt ttattaccct atcttattta tttatttatt catttatacc 900
aaccaaccat ggccacacaa gaaatcatcg a 931

<210> SEQ ID NO 16
<211> LENGTH: 908
<212> TYPE: DNA
<213> ORGANISM: Artificial Sequence
<220> FEATURE:
<223> OTHER INFORMATION: mutant CYP52A12

<400> SEQUENCE: 16
gtcgacttct cctttaggca atagaaaaag actaagggaa cagcgttttt acaggttgct 60
ttggttaatg tagtattttt tagtccaaca ttctgtgggt tgctctgggt ttctagaata 120
ggaaatcaca ggagaatgca aattcagatg gaagaacaaa gagataaaaa acaaaaaaaa 180
actgagtttt gcaccaatag aatgtttgat gatatcatcc actcgctaaa cgaatcatgt 240
gggtgatctt ctctttagtt ttggtctatc ataaaacaca tgaaagtgaa atccaaatac 300
actacactcc gggtattgtc cttcgtttta cggatgtctc attgtcttac ttttgaggtc 360
ataggagttg cctgtgagag atcacagaga ttatcacact cacatttatc gtagtttcct 420
atctcatgct gtgtgtctct ggttggttca tgagtttgga ttgttgtaca ttaaaggaat 480
cgctggaaag caaagctatt taaatttttt ctttgtcaca ggtacactaa cctgtaaaac 540
ttcactgcca cgccagtctt tcctgattgg gcaagtgcac aaactacaac ctgcaaaaca 600
gcactccgct tgtcacaggt tgtctcctct caaccaacaa aaaaataaga ttaaactttc 660
tttgctcatg catcaatcgg agttatctct gaaagagttg cctttgtgta atgtgtgcca 720
aactcaaact gcaaaactaa ccacagaatg atttccctca caattatata aactcaccca 780
catttccaca gaccgtaatt tcatgtctca ctttctcttt tgctcttctt ttacttagtc 840
aggtttgata acttcctttt ttattaccct atcttattta tttatttatt catttatacc 900
aaccaacc 908

<210> SEQ ID NO 17
<211> LENGTH: 493
<212> TYPE: DNA
<213> ORGANISM: Artificial Sequence
<220> FEATURE:
<223> OTHER INFORMATION: CYP52A12_Upstream

<400> SEQUENCE: 17
ggtcgaggaa gtggcattaa atccatgcga tgatcgcagg agatcagaat caaattgttg 60
ggttctagcg taacttcgtt aattacatga ggagtggagt aagcgtaata tgcgcgaagg 120
gctcagaacc gcacgtgact tcccctaaca ttgtagttaa gaggggaggg atcggagttt 180 ctttttggt tgtgcacgga gaaatcgttg aaaaggtggg gcacattttc atatgcgcta 240
atcttctttt tctttttatc acaggagaaa ctatcccacc cccacttcga aacacaatga 300
caactcctgc gtaacttgca aattcttgtc tgactaattg aaaactccgg acgagtcaga 360
cctccagtca aacggacaga cagacaaaca cttggtgcga tgttcatacc tacagacatg 420
tcaacgggtg ttagacgacg gtttcttgca aagacaggtg ttggcatctc gtacgatggc 480
aactgcagga ggt 493

<210> SEQ ID NO 18
<211> LENGTH: 750
<212> TYPE: DNA
<213> ORGANISM: Artificial Sequence
<220> FEATURE:
<223> OTHER INFORMATION: CYP52A12_Downstream

<400> SEQUENCE: 18
atggccacac aagaaatcat cgattctgta cttccgtact tgaccaaatg gtacactgtg 60
attactgcag cagtattagt cttccttatc tccacaaaca tcaagaacta cgtcaaggca 120
aagaaattga aatgtgtcga tccaccatac ttgaaggatg ccggtctcac tggtattctg 180
tctttgatcg ccgccatcaa ggccaagaac gacggtagat tggctaactt tgccgatgaa 240
gttttcgacg agtacccaaa ccacaccttc tacttgtctg ttgccggtgc tttgaagatt 300
gtcatgactg ttgacccaga aaacatcaag gctgtcttgg ccacccaatt cactgacttc 360
tccttgggta ccagacacgc ccactttgct cctttgttgg gtgacggtat cttcaccttg 420
gacggagaag gttggaagca ctccagagct atgttgagac cacagtttgc tagagaccag 480
attggacacg ttaaagcctt ggaaccacac atccaaatca tggctaagca gatcaagttg 540

```
aaccagggaa agactttcga tatccaagaa ttgttcttta gatttaccgt cgacaccgct    600

actgagttct tgtttggtga atccgttcac tccttgtacg atgaaaaatt gggcatccca    660

actccaaacg aaatcccagg aagagaaaac tttgccgctg ctttcaacgt ttcccaacac    720

tacttggcca ccagaagtta ctcccagact                                     750
```

<210> SEQ ID NO 19
<211> LENGTH: 20
<212> TYPE: DNA
<213> ORGANISM: Artificial Sequence
<220> FEATURE:
<223> OTHER INFORMATION: primer HYG-F

<400> SEQUENCE: 19

```
ctcggagggc gaagaatctc                                                 20
```

<210> SEQ ID NO 20
<211> LENGTH: 20
<212> TYPE: DNA
<213> ORGANISM: Artificial Sequence
<220> FEATURE:
<223> OTHER INFORMATION: primer HYG-R

<400> SEQUENCE: 20

```
caatgaccgc tgttatgcgg                                                 20
```

<210> SEQ ID NO 21
<211> LENGTH: 4115
<212> TYPE: DNA
<213> ORGANISM: Candida tropicalis

<400> SEQUENCE: 21

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat ttttttagtc ccagcattct    360

gtgggttgct ctgggtttct agaataggaa atcacaggag aatgcaaatt cagatggaag    420

aacaaagaga taaaaaacaa aaaaaaactg agttttgcac caatagaatg tttgatgata    480

tcatccactc gctaaacgaa tcatgtgggt gatcttctct ttagttttgg tctatcataa    540

aacacatgaa agtgaaatcc aaatacacta cactccgggt attgtccttc gttttacaga    600

tgtctcattg tcttactttt gaggtcatag gagttgcctg tgagagatca cagagattat    660

cacactcaca tttatcgtag tttcctatct catgctgtgt gtctctggtt ggttcatgag    720

tttggattgt tgtacattaa aggaatcgct ggaaagcaaa gctaactaaa ttttctttgt    780

cacaggtaca ctaacctgta aaacttcact gccacgccag tctttcctga ttgggcaagt    840

gcacaaacta caacctgcaa aacagcactc cgcttgtcac aggttgtctc ctctcaacca    900

acaaaaaaat aagattaaac tttctttgct catgcatcaa tcggagttat ctctgaaaga    960

gttgcctttg tgtaatgtgt gccaaactca aactgcaaaa ctaaccacag aatgatttcc   1020

ctcacaatta tataaactca cccacatttc cacagaccgt aatttcatgt ctcactttct   1080

cttttgctct tcttttactt agtcaggttt gataacttcc ttttttatta ccctatctta   1140

tttatttatt tattcattta taccaaccaa ccaaccatgg ccacacaaga aatcatcgat   1200
```

-continued

```
tctgtacttc cgtacttgac caaatggtac actgtgatta ctgcagcagt attagtcttc   1260
cttatctcca caaacatcaa gaactacgtc aaggcaaaga aattgaaatg tgtcgatcca   1320
ccatacttga aggatgccgg tctcactggt attctgtctt tgatcgccgc catcaaggcc   1380
aagaacgacg gtagattggc taactttgcc gatgaagttt tcgacgagta cccaaaccac   1440
accttctact tgtctgttgc cggtgctttg aagattgtca tgactgttga cccagaaaac   1500
atcaaggctg tcttggccac ccaattcact gacttctcct tgggtaccag acacgcccac   1560
tttgctcctt tgttgggtga cggtatcttc accttggacg gagaaggttg gaagcactcc   1620
agagctatgt tgagaccaca gtttgctaga gaccagattg gacacgttaa agccttggaa   1680
ccacacatcc aaatcatggc taagcagatc aagttgaacc agggaaagac tttcgatatc   1740
caagaattgt tctttagatt taccgtcgac accgctactg agttcttgtt tggtgaatcc   1800
gttcactcct tgtacgatga aaaattgggc atcccaactc caaacgaaat cccaggaaga   1860
gaaaactttg ccgctgcttt caacgtttcc caacactact tggccaccag aagttactcc   1920
cagacttttt actttttgac caaccctaag gaattcagag actgtaacgc caaggtccac   1980
cacttggcca agtactttgt caacaaggcc ttgaacttta ctcctgaaga actcgaagag   2040
aaatccaagt ccggttacgt tttcttgtac gaattggtta agcaaaccag agatccaaag   2100
gtcttgcaag atcaattgtt gaacattatg gttgccggaa gagacaccac tgccggtttg   2160
ttgtcctttg ctttgtttga attggctaga cacccagaga tgtggtccaa gttgagagaa   2220
gaaatcgaag ttaactttgg tgttggtgaa gactcccgcg ttgaagaaat taccttcgaa   2280
gccttgaaga gatgtgaata cttgaaggct atccttaacg aaaccttgcg tatgtaccca   2340
tctgttcctg tcaactttag aaccgccacc agagacacca ctttgccaag aggtggtggt   2400
gctaacggta ccgacccaat ctacattcct aaaggctcca ctgttgctta cgttgtctac   2460
aagacccacc gtttggaaga atactacggt aaggacgcta acgacttcag accagaaaga   2520
tggtttgaac catctactaa gaagttgggc tgggcttatg ttccattcaa cggtggtcca   2580
agagtctgct tgggtcaaca attcgccttg actgaagctt cttatgtgat cactagattg   2640
gcccagatgt ttgaaactgt ctcatctgat ccaggtctcg aataccctcc accaaagtgt   2700
attcacttga ccatgagtca caacgatggt gtctttgtca agatgtaaag tagtcgatgc   2760
tgggtattcg attacatgtg tataggaaga ttttggtttt ttattcgttc ttttttttaa   2820
tttttgttaa attagtttag agatttcatt aatacataga tgggtgctat ttccgaaact   2880
ttacttctat cccctgtatc ccttattatc cctctcagtc acatgattgc tgtaattgtc   2940
gtgcaggaca caaactccct aacggactta aaccataaac aagctcagaa ccataagccg   3000
acatcactcc ttcttctctc ttctccaacc aatagcatgg acagacccac cctcctatcc   3060
gaatcgaaga cccttattga ctccataccc acctggaagc ccctcaagcc acacacgtca   3120
tccagcccac ccatcaccac atccctctac tcgacaacgt ccaaagacgg cgagttctgg   3180
tgtgcccgga aatcagccat cccggccaca tacaagcagc cgttgattgc gtgcatactc   3240
ggcgagccca caatgggagc cacgcattcg gaccatgaag caaagtacat tcacgagatc   3300
acgggtgttt cagtgtcgca gattgagaag ttcgacgatg gatggaagta cgatctcgtt   3360
gcggattacg acttcggtgg gttgttatct aaacgaagat tctatgagac gcagcatgtg   3420
tttcggttcg aggattgtgc gtacgtcatg agtgtgcctt ttgatggacc caaggaggaa   3480
ggttacgtgg ttgggacgta cagatccatt gaaaggttga gctggggtaa agacggggac   3540
```

```
gtggagtgga ccatggcgac gacgtcggat cctggtgggt ttatcccgca atggataact   3600
cgattgagca tccctggagc aatcgcaaaa gatgtgccta gtgtattaaa ctacatacag   3660
aaataaaaac gtgtcttgat tcattggttt ggttcttgtt gggttccgag ccaatatttc   3720
acatcatctc ctaaattctc caagaatccc aacgtagcgt agtccagcac gccctctgag   3780
atcttattta atatcgactt ctcaaccacc ggtggaatcc cgttcagacc attgttacct   3840
gtagtgtgtt tgctcttgtt cttgatgaca atgatgtatt tgtcacgata cctgaaataa   3900
taaaacatcc agtcattgag cttattactc gtgaacttat gaaagaactc attcaagccg   3960
ttcccaaaaa acccagaatt gaagatcttg ctcaactggt catgcaagta gtagatcgcc   4020
atgatctgat actttaccaa gctatcctct ccaagttctc ccacgtacgg caagtacggc   4080
aacgagctct ggaagctttg ttgtttgggg tcata                              4115
```

<210> SEQ ID NO 22
<211> LENGTH: 4111
<212> TYPE: DNA
<213> ORGANISM: Artificial Sequence
<220> FEATURE:
<223> OTHER INFORMATION: mutant CYP52A12, -7_-4delACCA

<400> SEQUENCE: 22

```
catatgcgct aatcttcttt ttctttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat ttttttagtc ccagcattct    360
gtgggttgct ctgggtttct agaataggaa atcacaggag aatgcaaatt cagatggaag    420
aacaaagaga taaaaaacaa aaaaaaactg agttttgcac caatagaatg tttgatgata    480
tcatccactc gctaaacgaa tcatgtgggt gatcttctct ttagttttgg tctatcataa    540
aacacatgaa agtgaaatcc aaatacacta cactccgggt attgtccttc gttttacaga    600
tgtctcattg tcttactttt gaggtcatag gagttgcctg tgagagatca cagagattat    660
cacactcaca tttatcgtag tttcctatct catgctgtgt gtctctggtt ggttcatgag    720
tttggattgt tgtacattaa aggaatcgct ggaaagcaaa gctaactaaa ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900
acaaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcactttct   1080
cttttgctct tcttttactt agtcaggttt gataacttcc ttttttatta ccctatctta   1140
tttatttatt tattcattta taccaaccaa ccatggccac acaagaaatc atcgattctg   1200
tacttccgta cttgaccaaa tggtacactg tgattactgc agcagtatta gtcttcctta   1260
tctccacaaa catcaagaac tacgtcaagg caaagaaatt gaaatgtgtc gatccaccat   1320
acttgaagga tgccggtctc actggtattc tgtctttgat cgccgccatc aaggccaaga   1380
acgacggtag attggctaac tttgccgatg aagttttcga cgagtaccca aaccacacct   1440
tctacttgtc tgttgccggt gctttgaaga ttgtcatgac tgttgaccca gaaaacatca   1500
```

-continued

```
aggctgtctt ggccacccaa ttcactgact tctccttggg taccagacac gcccactttg   1560
ctcctttgtt gggtgacggt atcttcacct tggacggaga aggttggaag cactccagag   1620
ctatgttgag accacagttt gctagagacc agattggaca cgttaaagcc ttggaaccac   1680
acatccaaat catggctaag cagatcaagt tgaaccaggg aaagactttc gatatccaag   1740
aattgttctt tagatttacc gtcgacaccg ctactgagtt cttgtttggt gaatccgttc   1800
actccttgta cgatgaaaaa ttgggcatcc caactccaaa cgaaatccca ggaagagaaa   1860
actttgccgc tgctttcaac gtttcccaac actacttggc caccagaagt tactcccaga   1920
ctttttactt tttgaccaac cctaaggaat tcagagactg taacgccaag gtccaccact   1980
tggccaagta ctttgtcaac aaggccttga actttactcc tgaagaactc gaagagaaat   2040
ccaagtccgg ttacgttttc ttgtacgaat tggttaagca aaccagagat ccaaaggtct   2100
tgcaagatca attgttgaac attatggttg ccggaagaga caccactgcc ggtttgttgt   2160
cctttgcttt gtttgaattg gctagacacc cagagatgtg gtccaagttg agagaagaaa   2220
tcgaagttaa ctttggtgtt ggtgaagact cccgcgttga agaaattacc ttcgaagcct   2280
tgaagagatg tgaatacttg aaggctatcc ttaacgaaac cttgcgtatg tacccatctg   2340
ttcctgtcaa ctttagaacc gccaccagag acaccacttt gccaagaggt ggtggtgcta   2400
acggtaccga cccaatctac attcctaaag gctccactgt tgcttacgtt gtctacaaga   2460
cccaccgttt ggaagaatac tacggtaagg acgctaacga cttcagacca gaaagatggt   2520
ttgaaccatc tactaagaag ttgggctggg cttatgttcc attcaacggt ggtccaagag   2580
tctgcttggg tcaacaattc gccttgactg aagcttctta tgtgatcact agattggccc   2640
agatgtttga aactgtctca tctgatccag gtctcgaata ccctccacca aagtgtattc   2700
acttgaccat gagtcacaac gatggtgtct ttgtcaagat gtaaagtagt cgatgctggg   2760
tattcgatta catgtgtata ggaagatttt ggttttttat tcgttctttt ttttaatttt   2820
tgttaaatta gtttagagat ttcattaata catagatggg tgctatttcc gaaactttac   2880
ttctatcccc tgtatccctt attatccctc tcagtcacat gattgctgta attgtcgtgc   2940
aggacacaaa ctccctaacg gacttaaacc ataaacaagc tcagaaccat aagccgacat   3000
cactccttct tctctcttct ccaaccaata gcatggacag acccaccctc ctatccgaat   3060
cgaagaccct tattgactcc atacccacct ggaagcccct caagccacac acgtcatcca   3120
gcccacccat caccacatcc ctctactcga caacgtccaa agacggcgag ttctggtgtg   3180
cccggaaatc agccatcccg gccacataca agcagccgtt gattgcgtgc atactcggcg   3240
agcccacaat gggagccacg cattcggacc atgaagcaaa gtacattcac gagatcacgg   3300
gtgtttcagt gtcgcagatt gagaagttcg acgatggatg gaagtacgat ctcgttgcgg   3360
attacgactt cggtgggttg ttatctaaac gaagattcta tgagacgcag catgtgtttc   3420
ggttcgagga ttgtgcgtac gtcatgagtg tgccttttga tggacccaag gaggaaggtt   3480
acgtggttgg gacgtacaga tccattgaaa ggttgagctg gggtaaagac ggggacgtgg   3540
agtggaccat ggcgacgacg tcggatcctg gtgggtttat cccgcaatgg ataactcgat   3600
tgagcatccc tggagcaatc gcaaaagatg tgcctagtgt attaaactac atacagaaat   3660
aaaaacgtgt cttgattcat tggtttggtt cttgttgggt tccgagccaa tatttcacat   3720
catctcctaa attctccaag aatcccaacg tagcgtagtc cagcacgccc tctgagatct   3780
tatttaatat cgacttctca accaccggtg gaatcccgtt cagaccattg ttacctgtag   3840
```

-continued

```
tgtgtttgct cttgttcttg atgacaatga tgtatttgtc acgatacctg aaataataaa   3900

acatccagtc attgagctta ttactcgtga acttatgaaa gaactcattc aagccgttcc   3960

caaaaaaccc agaattgaag atcttgctca actggtcatg caagtagtag atcgccatga   4020

tctgatactt taccaagcta tcctctccaa gttctcccac gtacggcaag tacggcaacg   4080

agctctggaa gctttgttgt ttggggtcat a                                  4111
```

<210> SEQ ID NO 23
<211> LENGTH: 4113
<212> TYPE: DNA
<213> ORGANISM: Artificial Sequence
<220> FEATURE:
<223> OTHER INFORMATION: mutant CYP52A12, -412_-411AC>TT, -402insTT and -7_-4delACCA

<400> SEQUENCE: 23

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat ttttttagtc ccagcattct    360

gtgggttgct ctgggtttct agaataggaa atcacaggag aatgcaaatt cagatggaag    420

aacaaagaga taaaaaacaa aaaaaaactg agttttgcac caatagaatg tttgatgata    480

tcatccactc gctaaacgaa tcatgtgggt gatcttctct ttagttttgg tctatcataa    540

aacacatgaa agtgaaatcc aaatacacta cactccgggt attgtccttc gttttacaga    600

tgtctcattg tcttactttt gaggtcatag gagttgcctg tgagagatca cagagattat    660

cacactcaca tttatcgtag tttcctatct catgctgtgt gtctctggtt ggttcatgag    720

tttggattgt tgtacattaa aggaatcgct ggaaagcaaa gctatttaaa tttttctttt    780

gtcacaggta cactaacctg taaaacttca ctgccacgcc agtctttcct gattgggcaa    840

gtgcacaaac tacaacctgc aaaacagcac tccgcttgtc acaggttgtc tcctctcaac    900

caacaaaaaa ataagattaa actttctttg ctcatgcatc aatcggagtt atctctgaaa    960

gagttgcctt tgtgtaatgt gtgccaaact caaactgcaa aactaaccac agaatgattt   1020

ccctcacaat tatataaact cacccacatt tccacagacc gtaatttcat gtctcacttt   1080

ctcttttgct cttcttttac ttagtcaggt ttgataactt ccttttttat taccctatct   1140

tatttattta tttattcatt tataccaacc aaccatggcc acacaagaaa tcatcgattc   1200

tgtacttccg tacttgacca aatggtacac tgtgattact gcagcagtat tagtcttcct   1260

tatctccaca aacatcaaga actacgtcaa ggcaaagaaa ttgaaatgtg tcgatccacc   1320

atacttgaag gatgccggtc tcactggtat tctgtctttg atcgccgcca tcaaggccaa   1380

gaacgacggt agattggcta actttgccga tgaagttttc gacgagtacc caaaccacac   1440

cttctacttg tctgttgccg gtgctttgaa gattgtcatg actgttgacc cagaaaacat   1500

caaggctgtc ttggccaccc aattcactga cttctccttg ggtaccagac acgcccactt   1560

tgctcctttg ttgggtgacg gtatcttcac cttggacgga gaaggttgga agcactccag   1620

agctatgttg agaccacagt ttgctagaga ccagattgga cacgttaaag ccttggaacc   1680

acacatccaa atcatggcta agcagatcaa gttgaaccag ggaaagactt tcgatatcca   1740
```

agaattgttc tttagattta ccgtcgacac cgctactgag ttcttgtttg gtgaatccgt 1800
tcactccttg tacgatgaaa aattgggcat cccaactcca aacgaaatcc caggaagaga 1860
aaactttgcc gctgctttca acgtttccca acactacttg gccaccagaa gttactccca 1920
gactttttac tttttgacca accctaagga attcagagac tgtaacgcca aggtccacca 1980
cttggccaag tactttgtca acaaggcctt gaactttact cctgaagaac tcgaagagaa 2040
atccaagtcc ggttacgttt tcttgtacga attggttaag caaaccagag atccaaaggt 2100
cttgcaagat caattgttga acattatggt tgccggaaga gacaccactg ccggtttgtt 2160
gtcctttgct ttgtttgaat tggctagaca cccagagatg tggtccaagt tgagagaaga 2220
aatcgaagtt aactttggtg ttggtgaaga ctcccgcgtt gaagaaatta ccttcgaagc 2280
cttgaagaga tgtgaatact tgaaggctat ccttaacgaa accttgcgta tgtacccatc 2340
tgttcctgtc aactttagaa ccgccaccag agacaccact ttgccaagag gtggtggtgc 2400
taacggtacc gacccaatct acattcctaa aggctccact gttgcttacg ttgtctacaa 2460
gacccaccgt ttggaagaat actacggtaa ggacgctaac gacttcagac cagaaagatg 2520
gtttgaacca tctactaaga agttgggctg ggcttatgtt ccattcaacg gtggtccaag 2580
agtctgcttg ggtcaacaat tcgccttgac tgaagcttct tatgtgatca ctagattggc 2640
ccagatgttt gaaactgtct catctgatcc aggtctcgaa taccctccac caaagtgtat 2700
tcacttgacc atgagtcaca acgatggtgt ctttgtcaag atgtaaagta gtcgatgctg 2760
ggtattcgat tacatgtgta taggaagatt ttggtttttt attcgttctt ttttttaatt 2820
tttgttaaat tagtttagag atttcattaa tacatagatg ggtgctattt ccgaaacttt 2880
acttctatcc cctgtatccc ttattatccc tctcagtcac atgattgctg taattgtcgt 2940
gcaggacaca aactccctaa cggacttaaa ccataaacaa gctcagaacc ataagccgac 3000
atcactcctt cttctctctt ctccaaccaa tagcatggac agacccaccc tcctatccga 3060
atcgaagacc cttattgact ccatacccac ctggaagccc ctcaagccac acacgtcatc 3120
cagcccaccc atcaccacat ccctctactc gacaacgtcc aaagacggcg agttctggtg 3180
tgcccggaaa tcagccatcc cggccacata caagcagccg ttgattgcgt gcatactcgg 3240
cgagcccaca atgggagcca cgcattcgga ccatgaagca aagtacattc acgagatcac 3300
gggtgtttca gtgtcgcaga ttgagaagtt cgacgatgga tggaagtacg atctcgttgc 3360
ggattacgac ttcggtgggt tgttatctaa acgaagattc tatgagacgc agcatgtgtt 3420
tcggttcgag gattgtgcgt acgtcatgag tgtgcctttt gatggaccca aggaggaagg 3480
ttacgtggtt gggacgtaca gatccattga aaggttgagc tggggtaaag acggggacgt 3540
ggagtggacc atggcgacga cgtcggatcc tggtgggttt atcccgcaat ggataactcg 3600
attgagcatc cctggagcaa tcgcaaaaga tgtgcctagt gtattaaact acatacagaa 3660
ataaaaacgt gtcttgattc attggtttgg ttcttgttgg gttccgagcc aatatttcac 3720
atcatctcct aaattctcca agaatcccaa cgtagcgtag tccagcacgc cctctgagat 3780
cttatttaat atcgacttct caaccaccgg tggaatcccg ttcagaccat tgttacctgt 3840
agtgtgtttg ctcttgttct tgatgacaat gatgtatttg tcacgatacc tgaaataata 3900
aaacatccag tcattgagct tattactcgt gaacttatga aagaactcat tcaagccgtt 3960
cccaaaaaac ccagaattga agatcttgct caactggtca tgcaagtagt agatcgccat 4020
gatctgatac tttaccaagc tatcctctcc aagttctccc acgtacggca agtacggcaa 4080
cgagctctgg aagctttgtt gtttggggtc ata 4113

<210> SEQ ID NO 24
<211> LENGTH: 4113
<212> TYPE: DNA
<213> ORGANISM: Artificial Sequence
<220> FEATURE:
<223> OTHER INFORMATION: mutant CYP52A12, -579A>G, -412_-411AC>TT, -402insTT and -7_-4delACCA

<400> SEQUENCE: 24

```
catatgcgct aatcttcttt ttctttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat ttttttagtc ccagcattct    360
gtgggttgct ctgggtttct agaataggaa atcacaggag aatgcaaatt cagatggaag    420
aacaaagaga taaaaaacaa aaaaaaactg agttttgcac caatagaatg tttgatgata    480
tcatccactc gctaaacgaa tcatgtgggt gatcttctct ttagttttgg tctatcataa    540
aacacatgaa agtgaaatcc aaatacacta cactccgggt attgtccttc gttttacgga    600
tgtctcattg tcttactttt gaggtcatag gagttgcctg tgagagatca cagagattat    660
cacactcaca tttatcgtag tttcctatct catgctgtgt gtctctggtt ggttcatgag    720
tttggattgt tgtacattaa aggaatcgct ggaaagcaaa gctatttaaa tttttttcttt    780
gtcacaggta cactaacctg taaaacttca ctgccacgcc agtctttcct gattgggcaa    840
gtgcacaaac tacaacctgc aaaacagcac tccgcttgtc acaggttgtc tcctctcaac    900
caacaaaaaa ataagattaa actttctttg ctcatgcatc aatcggagtt atctctgaaa    960
gagttgcctt tgtgtaatgt gtgccaaact caaactgcaa aactaaccac agaatgattt   1020
ccctcacaat tatataaact cacccacatt tccacagacc gtaatttcat gtctcacttt   1080
ctcttttgct cttcttttac ttagtcaggt ttgataactt cctttttttat taccctatct   1140
tatttattta tttattcatt tataccaacc aaccatggcc acacaagaaa tcatcgattc   1200
tgtacttccg tacttgacca aatggtacac tgtgattact gcagcagtat tagtcttcct   1260
tatctccaca aacatcaaga actacgtcaa ggcaaagaaa ttgaaatgtg tcgatccacc   1320
atacttgaag gatgccggtc tcactggtat tctgtctttg atcgccgcca tcaaggccaa   1380
gaacgacggt agattggcta actttgccga tgaagttttc gacgagtacc caaaccacac   1440
cttctacttg tctgttgccg gtgctttgaa gattgtcatg actgttgacc cagaaaacat   1500
caaggctgtc ttggccaccc aattcactga cttctccttg ggtaccagac acgcccactt   1560
tgctcctttg ttgggtgacg gtatcttcac cttggacgga gaaggttgga agcactccag   1620
agctatgttg agaccacagt ttgctagaga ccagattgga cacgttaaag ccttggaacc   1680
acacatccaa atcatggcta agcagatcaa gttgaaccag ggaaagactt tcgatatcca   1740
agaattgttc tttagattta ccgtcgacac cgctactgag ttcttgtttg gtgaatccgt   1800
tcactccttg tacgatgaaa aattgggcat cccaactcca aacgaaatcc caggaagaga   1860
aaactttgcc gctgctttca acgtttccca acactacttg gccaccagaa gttactccca   1920
gactttttac tttttgacca accctaagga attcagagac tgtaacgcca aggtccacca   1980
cttggccaag tactttgtca acaaggcctt gaactttact cctgaagaac tcgaagagaa   2040
```

atccaagtcc ggttacgttt tcttgtacga attggttaag caaaccagag atccaaaggt 2100
cttgcaagat caattgttga acattatggt tgccggaaga gacaccactg ccggtttgtt 2160
gtcctttgct ttgtttgaat tggctagaca cccagagatg tggtccaagt tgagagaaga 2220
aatcgaagtt aactttggtg ttggtgaaga ctcccgcgtt gaagaaatta ccttcgaagc 2280
cttgaagaga tgtgaatact tgaaggctat ccttaacgaa accttgcgta tgtacccatc 2340
tgttcctgtc aactttagaa ccgccaccag agacaccact ttgccaagag gtggtggtgc 2400
taacggtacc gacccaatct acattcctaa aggctccact gttgcttacg ttgtctacaa 2460
gacccaccgt ttggaagaat actacggtaa ggacgctaac gacttcagac cagaaagatg 2520
gtttgaacca tctactaaga agttgggctg ggcttatgtt ccattcaacg gtggtccaag 2580
agtctgcttg ggtcaacaat tcgccttgac tgaagcttct tatgtgatca ctagattggc 2640
ccagatgttt gaaactgtct catctgatcc aggtctcgaa taccctccac caaagtgtat 2700
tcacttgacc atgagtcaca acgatggtgt ctttgtcaag atgtaaagta gtcgatgctg 2760
ggtattcgat tacatgtgta taggaagatt ttggtttttt attcgttctt ttttttaatt 2820
tttgttaaat tagtttagag atttcattaa tacatagatg ggtgctattt ccgaaacttt 2880
acttctatcc cctgtatccc ttattatccc tctcagtcac atgattgctg taattgtcgt 2940
gcaggacaca aactccctaa cggacttaaa ccataaacaa gctcagaacc ataagccgac 3000
atcactcctt cttctctctt ctccaaccaa tagcatggac agacccaccc tcctatccga 3060
atcgaagacc cttattgact ccatacccac ctggaagccc ctcaagccac acacgtcatc 3120
cagcccaccc atcaccacat ccctctactc gacaacgtcc aaagacggcg agttctggtg 3180
tgcccggaaa tcagccatcc cggccacata caagcagccg ttgattgcgt gcatactcgg 3240
cgagcccaca atgggagcca cgcattcgga ccatgaagca aagtacattc acgagatcac 3300
gggtgtttca gtgtcgcaga ttgagaagtt cgacgatgga tggaagtacg atctcgttgc 3360
ggattacgac ttcggtgggt tgttatctaa acgaagattc tatgagacgc agcatgtgtt 3420
tcggttcgag gattgtgcgt acgtcatgag tgtgcctttt gatggaccca aggaggaagg 3480
ttacgtggtt gggacgtaca gatccattga aaggttgagc tggggtaaag acggggacgt 3540
ggagtggacc atggcgacga cgtcggatcc tggtgggttt atcccgcaat ggataactcg 3600
attgagcatc cctggagcaa tcgcaaaaga tgtgcctagt gtattaaact acatacagaa 3660
ataaaaacgt gtcttgattc attggtttgg ttcttgttgg gttccgagcc aatatttcac 3720
atcatctcct aaattctcca agaatcccaa cgtagcgtag tccagcacgc cctctgagat 3780
cttatttaat atcgacttct caaccaccgg tggaatcccg ttcagaccat tgttacctgt 3840
agtgtgtttg ctcttgttct tgatgacaat gatgtatttg tcacgatacc tgaaataata 3900
aaacatccag tcattgagct tattactcgt gaacttatga aagaactcat tcaagccgtt 3960
cccaaaaaac ccagaattga agatcttgct caactggtca tgcaagtagt agatcgccat 4020
gatctgatac tttaccaagc tatcctctcc aagttctccc acgtacggca agtacggcaa 4080
cgagctctgg aagctttgtt gtttggggtc ata 4113

<210> SEQ ID NO 25
<211> LENGTH: 4111
<212> TYPE: DNA
<213> ORGANISM: Artificial Sequence
<220> FEATURE:
<223> OTHER INFORMATION: mutant CYP52A12, -831delT, -825C>A, -823delG,
-579A>G,

<400> SEQUENCE: 25

```
catatgcgct aatcttcttt ttctttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat tttttagtcc aacattctgt    360
gggttgctct gggtttctag aataggaaat cacaggagaa tgcaaattca gatggaagaa    420
caaagagata aaaaacaaaa aaaaactgag ttttgcacca atagaatgtt tgatgatatc    480
atccactcgc taaacgaatc atgtgggtga tcttctcttt agttttggtc tatcataaaa    540
cacatgaaag tgaaatccaa atacactaca ctccgggtat tgtccttcgt tttacggatg    600
tctcattgtc ttacttttga ggtcatagga gttgcctgtg agagatcaca gagattatca    660
cactcacatt tatcgtagtt tcctatctca tgctgtgtgt ctctggttgg ttcatgagtt    720
tggattgttg tacattaaag gaatcgctgg aaagcaaagc tatttaaatt ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900
acaaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcactttct   1080
cttttgctct tcttttactt agtcaggttt gataacttcc tttttatta ccctatctta   1140
tttatttatt tattcattta taccaaccaa ccatggccac acaagaaatc atcgattctg   1200
tacttccgta cttgaccaaa tggtacactg tgattactgc agcagtatta gtcttcctta   1260
tctccacaaa catcaagaac tacgtcaagg caaagaaatt gaaatgtgtc gatccaccat   1320
acttgaagga tgccggtctc actggtattc tgtctttgat cgccgccatc aaggccaaga   1380
acgacggtag attggctaac tttgccgatg aagttttcga cgagtaccca aaccacacct   1440
tctacttgtc tgttgccggt gctttgaaga ttgtcatgac tgttgaccca gaaaacatca   1500
aggctgtctt ggccacccaa ttcactgact tctccttggg taccagacac gcccactttg   1560
ctcctttgtt gggtgacggt atcttcacct tggacggaga aggttggaag cactccagag   1620
ctatgttgag accacagttt gctagagacc agattggaca cgttaaagcc ttggaaccac   1680
acatccaaat catggctaag cagatcaagt tgaaccaggg aaagactttc gatatccaag   1740
aattgttctt tagatttacc gtcgacaccg ctactgagtt cttgtttggt gaatccgttc   1800
actccttgta cgatgaaaaa ttgggcatcc caactccaaa cgaaatccca ggaagagaaa   1860
actttgccgc tgctttcaac gtttcccaac actacttggc caccagaagt tactcccaga   1920
ctttttactt tttgaccaac cctaaggaat tcagagactg taacgccaag gtccaccact   1980
tggccaagta ctttgtcaac aaggccttga actttactcc tgaagaactc gaagagaaat   2040
ccaagtccgg ttacgttttc ttgtacgaat tggttaagca aaccagagat ccaaaggtct   2100
tgcaagatca attgttgaac attatggttg ccggaagaga caccactgcc ggtttgttgt   2160
cctttgcttt gtttgaattg gctagacacc cagagatgtg gtccaagttg agagaagaaa   2220
tcgaagttaa ctttggtgtt ggtgaagact cccgcgttga agaaattacc ttcgaagcct   2280
```

-continued

```
tgaagagatg tgaatacttg aaggctatcc ttaacgaaac cttgcgtatg tacccatctg   2340

ttcctgtcaa ctttagaacc gccaccagag acaccacttt gccaagaggt ggtggtgcta   2400

acggtaccga cccaatctac attcctaaag gctccactgt tgcttacgtt gtctacaaga   2460

cccaccgttt ggaagaatac tacggtaagg acgctaacga cttcagacca gaaagatggt   2520

ttgaaccatc tactaagaag ttgggctggg cttatgttcc attcaacggt ggtccaagag   2580

tctgcttggg tcaacaattc gccttgactg aagcttctta tgtgatcact agattggccc   2640

agatgtttga aactgtctca tctgatccag gtctcgaata ccctccacca aagtgtattc   2700

acttgaccat gagtcacaac gatggtgtct ttgtcaagat gtaaagtagt cgatgctggg   2760

tattcgatta catgtgtata ggaagatttt ggttttttat tcgttctttt ttttaatttt   2820

tgttaaatta gtttagagat ttcattaata catagatggg tgctatttcc gaaactttac   2880

ttctatcccc tgtatccctt attatccctc tcagtcacat gattgctgta attgtcgtgc   2940

aggacacaaa ctccctaacg gacttaaacc ataaacaagc tcagaaccat aagccgacat   3000

cactccttct tctctcttct ccaaccaata gcatggacag acccaccctc ctatccgaat   3060

cgaagaccct tattgactcc atacccacct ggaagcccct caagccacac acgtcatcca   3120

gcccacccat caccacatcc ctctactcga caacgtccaa agacggcgag ttctggtgtg   3180

cccggaaatc agccatcccg gccacataca agcagccgtt gattgcgtgc atactcggcg   3240

agcccacaat gggagccacg cattcggacc atgaagcaaa gtacattcac gagatcacgg   3300

gtgtttcagt gtcgcagatt gagaagttcg acgatggatg gaagtacgat ctcgttgcgg   3360

attacgactt cggtgggttg ttatctaaac gaagattcta tgagacgcag catgtgtttc   3420

ggttcgagga ttgtgcgtac gtcatgagtg tgccttttga tggacccaag gaggaaggtt   3480

acgtggttgg gacgtacaga tccattgaaa ggttgagctg gggtaaagac ggggacgtgg   3540

agtggaccat ggcgacgacg tcggatcctg gtgggtttat cccgcaatgg ataactcgat   3600

tgagcatccc tggagcaatc gcaaaagatg tgcctagtgt attaaactac atacagaaat   3660

aaaaacgtgt cttgattcat tggtttggtt cttgttgggt tccgagccaa tatttcacat   3720

catctcctaa attctccaag aatcccaacg tagcgtagtc cagcacgccc tctgagatct   3780

tatttaatat cgacttctca accaccggtg gaatcccgtt cagaccattg ttacctgtag   3840

tgtgtttgct cttgttcttg atgacaatga tgtatttgtc acgatacctg aaataataaa   3900

acatccagtc attgagctta ttactcgtga acttatgaaa gaactcattc aagccgttcc   3960

caaaaaaccc agaattgaag atcttgctca actggtcatg caagtagtag atcgccatga   4020

tctgatactt taccaagcta tcctctccaa gttctcccac gtacggcaag tacggcaacg   4080

agctctggaa gctttgttgt ttggggtcat a                                  4111
```

<210> SEQ ID NO 26
<211> LENGTH: 4111
<212> TYPE: DNA
<213> ORGANISM: Artificial Sequence
<220> FEATURE:
<223> OTHER INFORMATION: mutant CYP52A12, containing

<400> SEQUENCE: 26

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240
```

-continued

```
cgtacgatgg caactgcagg aggtgtcgac ttctccttta ggcaatagaa aaagactaag    300
ggaacagcgt ttttacaggt tgctttggtt aatgtagtat tttttagtcc aacattctgt    360
gggttgctct gggtttctag aataggaaat cacaggagaa tgcaaattca gatggaagaa    420
caaagagata aaaaacaaaa aaaaactgag ttttgcacca atagaatgtt tgatgatatc    480
atccactcgc taaacgaatc atgtgggtga tcttctcttt agttttggtc tatcataaaa    540
cacatgaaag tgaaatccaa atacactaca ctccgggtat tgtccttcgt tttacggatg    600
tctcattgtc ttacttttga ggtcatagga gttgcctgtg agagatcaca gagattatca    660
cactcacatt tatcgtagtt tcctatctca tgctgtgtgt ctctggttgg ttcatgagtt    720
tggattgttg tacattaaag gaatcgctgg aaagcaaagc tatttaaatt ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900
acaaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcactttct   1080
cttttgctct tcttttactt agtcaggttt gataacttcc tttttatta ccctatctta   1140
tttatttatt tattcattta taccaaccaa ccatggccac acaagaaatc atcgattctg   1200
tacttccgta cttgaccaaa tggtacactg tgattactgc agcagtatta gtcttcctta   1260
tctccacaaa catcaagaac tacgtcaagg caaagaaatt gaaatgtgtc gatccaccat   1320
acttgaagga tgccggtctc actggtattc tgtctttgat cgccgccatc aaggccaaga   1380
acgacggtag attggctaac tttgccgatg aagttttcga cgagtaccca aaccacacct   1440
tctacttgtc tgttgccggt gctttgaaga ttgtcatgac tgttgaccca gaaaacatca   1500
aggctgtctt ggccacccaa ttcactgact tctccttggg taccagacac gcccactttg   1560
ctcctttgtt gggtgacggt atcttcacct tggacggaga aggttggaag cactccagag   1620
ctatgttgag accacagttt gctagagacc agattggaca cgttaaagcc ttggaaccac   1680
acatccaaat catggctaag cagatcaagt tgaaccaggg aaagactttc gatatccaag   1740
aattgttctt tagatttacc gtcgacaccg ctactgagtt cttgtttggt gaatccgttc   1800
actccttgta cgatgaaaaa ttgggcatcc caactccaaa cgaaatccca ggaagagaaa   1860
actttgccgc tgctttcaac gtttcccaac actacttggc caccagaagt tactcccaga   1920
ctttttactt tttgaccaac cctaaggaat tcagagactg taacgccaag gtccaccact   1980
tggccaagta ctttgtcaac aaggccttga actttactcc tgaagaactc gaagagaaat   2040
ccaagtccgg ttacgttttc ttgtacgaat tggttaagca aaccagagat ccaaaggtct   2100
tgcaagatca attgttgaac attatggttg ccggaagaga caccactgcc ggtttgttgt   2160
cctttgcttt gtttgaattg gctagacacc cagagatgtg gtccaagttg agagaagaaa   2220
tcgaagttaa ctttggtgtt ggtgaagact cccgcgttga agaaattacc ttcgaagcct   2280
tgaagagatg tgaatacttg aaggctatcc ttaacgaaac cttgcgtatg tacccatctg   2340
ttcctgtcaa ctttagaacc gccaccagag acaccacttt gccaagaggt ggtggtgcta   2400
acggtaccga cccaatctac attcctaaag gctccactgt tgcttacgtt gtctacaaga   2460
cccaccgttt ggaagaatac tacggtaagg acgctaacga cttcagacca gaaagatggt   2520
ttgaaccatc tactaagaag ttgggctggg cttatgttcc attcaacggt ggtccaagag   2580
```

```
tctgcttggg tcaacaattc gccttgactg aagcttctta tgtgatcact agattggccc   2640
agatgtttga aactgtctca tctgatccag gtctcgaata ccctccacca aagtgtattc   2700
acttgaccat gagtcacaac gatggtgtct ttgtcaagat gtaaagtagt cgatgctggg   2760
tattcgatta catgtgtata ggaagatttt ggttttttat tcgttctttt ttttaatttt   2820
tgttaaatta gtttagagat ttcattaata catagatggg tgctatttcc gaaactttac   2880
ttctatcccc tgtatccctt attatccctc tcagtcacat gattgctgta attgtcgtgc   2940
aggacacaaa ctccctaacg gacttaaacc ataaacaagc tcagaaccat aagccgacat   3000
cactccttct tctctcttct ccaaccaata gcatggacag acccaccctc ctatccgaat   3060
cgaagaccct tattgactcc atacccacct ggaagcccct caagccacac acgtcatcca   3120
gcccacccat caccacatcc ctctactcga caacgtccaa agacggcgag ttctggtgtg   3180
cccggaaatc agccatcccg gccacataca agcagccgtt gattgcgtgc atactcggcg   3240
agcccacaat gggagccacg cattcggacc atgaagcaaa gtacattcac gagatcacgg   3300
gtgtttcagt gtcgcagatt gagaagttcg acgatggatg gaagtacgat ctcgttgcgg   3360
attacgactt cggtgggttg ttatctaaac gaagattcta tgagacgcag catgtgtttc   3420
ggttcgagga ttgtgcgtac gtcatgagtg tgccttttga tggacccaag gaggaaggtt   3480
acgtggttgg gacgtacaga tccattgaaa ggttgagctg gggtaaagac ggggacgtgg   3540
agtggaccat ggcgacgacg tcggatcctg gtgggtttat cccgcaatgg ataactcgat   3600
tgagcatccc tggagcaatc gcaaaagatg tgcctagtgt attaaactac atacagaaat   3660
aaaaacgtgt cttgattcat tggtttggtt cttgttgggt tccgagccaa tatttcacat   3720
catctcctaa attctccaag aatcccaacg tagcgtagtc cagcacgccc tctgagatct   3780
tatttaatat cgacttctca accaccggtg gaatcccgtt cagaccattg ttacctgtag   3840
tgtgtttgct cttgttcttg atgacaatga tgtatttgtc acgatacctg aaataataaa   3900
acatccagtc attgagctta ttactcgtga acttatgaaa gaactcattc aagccgttcc   3960
caaaaaaccc agaattgaag atcttgctca actggtcatg caagtagtag atcgccatga   4020
tctgatactt taccaagcta tcctctccaa gttctcccac gtacggcaag tacggcaacg   4080
agctctggaa gctttgttgt ttggggtcat a                                  4111
```

<210> SEQ ID NO 27
<211> LENGTH: 1172
<212> TYPE: DNA
<213> ORGANISM: Artificial Sequence
<220> FEATURE:
<223> OTHER INFORMATION: 1170_1173delACCA

<400> SEQUENCE: 27

```
catatgcgct aatcttcttt ttctttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat ttttttagtc ccagcattct    360
gtgggttgct ctgggtttct agaataggaa atcacaggag aatgcaaatt cagatggaag    420
aacaaagaga taaaaaacaa aaaaaaactg agttttgcac caatagaatg tttgatgata    480
tcatccactc gctaaacgaa tcatgtgggt gatcttctct ttagttttgg tctatcataa    540
```

aacacatgaa agtgaaatcc aaatacacta cactccgggt attgtccttc gttttacaga 600
tgtctcattg tcttactttt gaggtcatag gagttgcctg tgagagatca cagagattat 660
cacactcaca tttatcgtag tttcctatct catgctgtgt gtctctggtt ggttcatgag 720
tttggattgt tgtacattaa aggaatcgct ggaaagcaaa gctaactaaa ttttctttgt 780
cacaggtaca ctaacctgta aaacttcact gccacgccag tctttcctga ttgggcaagt 840
gcacaaacta caacctgcaa aacagcactc cgcttgtcac aggttgtctc ctctcaacca 900
acaaaaaaat aagattaaac tttctttgct catgcatcaa tcggagttat ctctgaaaga 960
gttgcctttg tgtaatgtgt gccaaactca aactgcaaaa ctaaccacag aatgatttcc 1020
ctcacaatta tataaactca cccacatttc cacagaccgt aatttcatgt ctcactttct 1080
cttttgctct tcttttactt agtcaggttt gataacttcc ttttttatta ccctatctta 1140
tttatttatt tattcattta taccaaccaa cc 1172

<210> SEQ ID NO 28
<211> LENGTH: 1174
<212> TYPE: DNA
<213> ORGANISM: Artificial Sequence
<220> FEATURE:
<223> OTHER INFORMATION: 765_766AC>TT, 774insTT and 1170_1173delACCA

<400> SEQUENCE: 28
catatgcgct aatcttcttt ttctttttat cacaggagaa actatcccac ccccacttcg 60
aaacacaatg acaactcctg cgtaacttgc aaattcttgt ctgactaatt gaaaactccg 120
gacgagtcag acctccagtc aaacggacag acagacaaac acttggtgcg atgttcatac 180
ctacagacat gtcaacgggt gttagacgac ggtttcttgc aaagacaggt gttggcatct 240
cgtacgatgg caactgcagg aggtgtcgac ttctccttta ggcaatagaa aaagactaag 300
agaacagcgt ttttacaggt tgcattggtt aatgtagtat ttttttagtc ccagcattct 360
gtgggttgct ctgggtttct agaataggaa atcacaggag aatgcaaatt cagatggaag 420
aacaaagaga taaaaaacaa aaaaaaactg agttttgcac caatagaatg tttgatgata 480
tcatccactc gctaaacgaa tcatgtgggt gatcttctct ttagttttgg tctatcataa 540
aacacatgaa agtgaaatcc aaatacacta cactccgggt attgtccttc gttttacaga 600
tgtctcattg tcttactttt gaggtcatag gagttgcctg tgagagatca cagagattat 660
cacactcaca tttatcgtag tttcctatct catgctgtgt gtctctggtt ggttcatgag 720
tttggattgt tgtacattaa aggaatcgct ggaaagcaaa gctatttaaa ttttttcttt 780
gtcacaggta cactaacctg taaaacttca ctgccacgcc agtctttcct gattgggcaa 840
gtgcacaaac tacaacctgc aaaacagcac tccgcttgtc acaggttgtc tcctctcaac 900
caacaaaaaa ataagattaa actttctttg ctcatgcatc aatcggagtt atctctgaaa 960
gagttgcctt tgtgtaatgt gtgccaaact caaactgcaa aactaaccac agaatgattt 1020
ccctcacaat tatataaact cacccacatt tccacagacc gtaatttcat gtctcacttt 1080
ctcttttgct cttcttttac ttagtcaggt ttgataactt ccttttttat taccctatct 1140
tatttattta tttattcatt tataccaacc aacc 1174

<210> SEQ ID NO 29
<211> LENGTH: 1174
<212> TYPE: DNA
<213> ORGANISM: Artificial Sequence
<220> FEATURE:

<223> OTHER INFORMATION: 598A>G, 765_766AC>TT, 774insTT and 1170_1173delACCA

<400> SEQUENCE: 29

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat ttttttagtc ccagcattct    360

gtgggttgct ctgggtttct agaataggaa atcacaggag aatgcaaatt cagatggaag    420

aacaaagaga taaaaaaacaa aaaaaaactg agttttgcac caatagaatg tttgatgata    480

tcatccactc gctaaacgaa tcatgtgggt gatcttctct ttagttttgg tctatcataa    540

aacacatgaa agtgaaatcc aaatacacta cactccgggt attgtccttc gttttacgga    600

tgtctcattg tcttactttt gaggtcatag gagttgcctg tgagagatca cagagattat    660

cacactcaca tttatcgtag tttcctatct catgctgtgt gtctctggtt ggttcatgag    720

tttggattgt tgtacattaa aggaatcgct ggaaagcaaa gctatttaaa ttttttcttt    780

gtcacaggta cactaacctg taaaacttca ctgccacgcc agtctttcct gattgggcaa    840

gtgcacaaac tacaacctgc aaaacagcac tccgcttgtc acaggttgtc tcctctcaac    900

caacaaaaaa ataagattaa actttctttg ctcatgcatc aatcggagtt atctctgaaa    960

gagttgcctt tgtgtaatgt gtgccaaact caaactgcaa aactaaccac agaatgattt   1020

ccctcacaat tatataaact cacccacatt tccacagacc gtaatttcat gtctcacttt   1080

ctcttttgct cttcttttac ttagtcaggt ttgataactt cctttttat taccctatct   1140

tatttattta tttattcatt tataccaacc aacc                              1174
```

<210> SEQ ID NO 30
<211> LENGTH: 1172
<212> TYPE: DNA
<213> ORGANISM: Artificial Sequence
<220> FEATURE:
<223> OTHER INFORMATION: 346delT, 352C>A, 354delG, 598A>G, 765_766AC>TT, 774insTT and 1170_1173delACCA

<400> SEQUENCE: 30

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat tttttagtcc aacattctgt    360

gggttgctct gggtttctag aataggaaat cacaggagaa tgcaaattca gatggaagaa    420

caaagagata aaaaacaaaa aaaaactgag ttttgcacca atagaatgtt tgatgatatc    480

atccactcgc taaacgaatc atgtgggtga tcttctcttt agttttggtc tatcataaaa    540

cacatgaaag tgaaatccaa atacactaca ctccgggtat tgtccttcgt tttacggatg    600

tctcattgtc ttacttttga ggtcatagga gttgcctgtg agagatcaca gagattatca    660

cactcacatt tatcgtagtt tcctatctca tgctgtgtgt ctctggttgg ttcatgagtt    720
```

```
tggattgttg tacattaaag gaatcgctgg aaagcaaagc tatttaaatt ttttctttgt    780

cacaggtaca ctaacctgta aaacttcact gccacgccag tctttcctga ttgggcaagt    840

gcacaaacta caacctgcaa aacagcactc cgcttgtcac aggttgtctc ctctcaacca    900

acaaaaaaat aagattaaac tttctttgct catgcatcaa tcggagttat ctctgaaaga    960

gttgcctttg tgtaatgtgt gccaaactca aactgcaaaa ctaaccacag aatgatttcc   1020

ctcacaatta tataaactca cccacatttc cacagaccgt aatttcatgt ctcactttct   1080

cttttgctct tcttttactt agtcaggttt gataacttcc ttttttatta ccctatctta   1140

tttatttatt tattcattta taccaaccaa cc                                 1172


<210> SEQ ID NO 31
<211> LENGTH: 1172
<212> TYPE: DNA
<213> ORGANISM: Artificial Sequence
<220> FEATURE:
<223> OTHER INFORMATION: 301A>G, 324A>T, 346delT, 352C>A, 354delG,
      598A>G, 765_766AC>TT, 774insTT, and 1170_1173delACCA

<400> SEQUENCE: 31

catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

ggaacagcgt tttacaggt tgctttggtt aatgtagtat tttttagtcc aacattctgt    360

gggttgctct gggtttctag aataggaaat cacaggagaa tgcaaattca gatggaagaa    420

caaagagata aaaaacaaaa aaaaactgag ttttgcacca atagaatgtt tgatgatatc    480

atccactcgc taaacgaatc atgtgggtga tcttctcttt agttttggtc tatcataaaa    540

cacatgaaag tgaaatccaa atacactaca ctccgggtat tgtccttcgt tttacggatg    600

tctcattgtc ttacttttga ggtcatagga gttgcctgtg agagatcaca gagattatca    660

cactcacatt tatcgtagtt tcctatctca tgctgtgtgt ctctggttgg ttcatgagtt    720

tggattgttg tacattaaag gaatcgctgg aaagcaaagc tatttaaatt ttttctttgt    780

cacaggtaca ctaacctgta aaacttcact gccacgccag tctttcctga ttgggcaagt    840

gcacaaacta caacctgcaa aacagcactc cgcttgtcac aggttgtctc ctctcaacca    900

acaaaaaaat aagattaaac tttctttgct catgcatcaa tcggagttat ctctgaaaga    960

gttgcctttg tgtaatgtgt gccaaactca aactgcaaaa ctaaccacag aatgatttcc   1020

ctcacaatta tataaactca cccacatttc cacagaccgt aatttcatgt ctcactttct   1080

cttttgctct tcttttactt agtcaggttt gataacttcc ttttttatta ccctatctta   1140

tttatttatt tattcattta taccaaccaa cc                                 1172


<210> SEQ ID NO 32
<211> LENGTH: 908
<212> TYPE: DNA
<213> ORGANISM: Artificial Sequence
<220> FEATURE:
<223> OTHER INFORMATION: 1170_1173delACCA

<400> SEQUENCE: 32

gtcgacttct cctttaggca atagaaaaag actaagagaa cagcgttttt acaggttgca     60
```

ttggttaatg tagtattttt ttagtcccag cattctgtgg gttgctctgg gtttctagaa 120
taggaaatca caggagaatg caaattcaga tggaagaaca aagagataaa aaacaaaaaa 180
aaactgagtt ttgcaccaat agaatgtttg atgatatcat ccactcgcta aacgaatcat 240
gtgggtgatc ttctctttag ttttggtcta tcataaaaca catgaaagtg aaatccaaat 300
acactacact ccgggtattg tccttcgttt tacagatgtc tcattgtctt acttttgagg 360
tcataggagt tgcctgtgag agatcacaga gattatcaca ctcacattta tcgtagtttc 420
ctatctcatg ctgtgtgtct ctggttggtt catgagtttg gattgttgta cattaaagga 480
atcgctggaa agcaaagcta actaaatttt ctttgtcaca ggtacactaa cctgtaaaac 540
ttcactgcca cgccagtctt tcctgattgg gcaagtgcac aaactacaac ctgcaaaaca 600
gcactccgct tgtcacaggt tgtctcctct caaccaacaa aaaaataaga ttaaactttc 660
tttgctcatg catcaatcgg agttatctct gaaagagttg cctttgtgta atgtgtgcca 720
aactcaaact gcaaaactaa ccacagaatg atttccctca caattatata aactcaccca 780
catttccaca gaccgtaatt tcatgtctca ctttctcttt tgctcttctt ttacttagtc 840
aggtttgata acttcctttt ttattaccct atcttattta tttatttatt catttatacc 900
aaccaacc 908

<210> SEQ ID NO 33
<211> LENGTH: 910
<212> TYPE: DNA
<213> ORGANISM: Artificial Sequence
<220> FEATURE:
<223> OTHER INFORMATION: 765_766AC>TT, 774insTT and 1170_1173delACCA

<400> SEQUENCE: 33
gtcgacttct cctttaggca atagaaaaag actaagagaa cagcgttttt acaggttgca 60
ttggttaatg tagtattttt ttagtcccag cattctgtgg gttgctctgg gtttctagaa 120
taggaaatca caggagaatg caaattcaga tggaagaaca aagagataaa aaacaaaaaa 180
aaactgagtt ttgcaccaat agaatgtttg atgatatcat ccactcgcta aacgaatcat 240
gtgggtgatc ttctctttag ttttggtcta tcataaaaca catgaaagtg aaatccaaat 300
acactacact ccgggtattg tccttcgttt tacagatgtc tcattgtctt acttttgagg 360
tcataggagt tgcctgtgag agatcacaga gattatcaca ctcacattta tcgtagtttc 420
ctatctcatg ctgtgtgtct ctggttggtt catgagtttg gattgttgta cattaaagga 480
atcgctggaa agcaaagcta tttaaatttt ttctttgtca caggtacact aacctgtaaa 540
acttcactgc cacgccagtc tttcctgatt gggcaagtgc acaaactaca acctgcaaaa 600
cagcactccg cttgtcacag gttgtctcct ctcaaccaac aaaaaaataa gattaaactt 660
tctttgctca tgcatcaatc ggagttatct ctgaaagagt tgcctttgtg taatgtgtgc 720
caaactcaaa ctgcaaaact aaccacagaa tgatttccct cacaattata taaactcacc 780
cacatttcca cagaccgtaa tttcatgtct cactttctct tttgctcttc ttttacttag 840
tcaggtttga taacttcctt ttttattacc ctatcttatt tatttattta ttcatttata 900
ccaaccaacc 910

<210> SEQ ID NO 34
<211> LENGTH: 910
<212> TYPE: DNA
<213> ORGANISM: Artificial Sequence
<220> FEATURE:

<223> OTHER INFORMATION: 598A>G, 765_766AC>TT, 774insTT and
1170_1173delACCA

<400> SEQUENCE: 34
gtcgacttct cctttaggca atagaaaaag actaagagaa cagcgttttt acaggttgca 60
ttggttaatg tagtattttt ttagtcccag cattctgtgg gttgctctgg gtttctagaa 120
taggaaatca caggagaatg caaattcaga tggaagaaca aagagataaa aaacaaaaaa 180
aaactgagtt ttgcaccaat agaatgtttg atgatatcat ccactcgcta aacgaatcat 240
gtgggtgatc ttctctttag ttttggtcta tcataaaaca catgaaagtg aaatccaaat 300
acactacact ccgggtattg tccttcgttt tacggatgtc tcattgtctt acttttgagg 360
tcataggagt tgcctgtgag agatcacaga gattatcaca ctcacattta tcgtagtttc 420
ctatctcatg ctgtgtgtct ctggttggtt catgagtttg gattgttgta cattaaagga 480
atcgctggaa agcaaagcta tttaaatttt ttctttgtca caggtacact aacctgtaaa 540
acttcactgc cacgccagtc tttcctgatt gggcaagtgc acaaactaca acctgcaaaa 600
cagcactccg cttgtcacag gttgtctcct ctcaaccaac aaaaaaataa gattaaactt 660
tctttgctca tgcatcaatc ggagttatct ctgaaagagt tgcctttgtg taatgtgtgc 720
caaactcaaa ctgcaaaact aaccacagaa tgatttccct cacaattata taaactcacc 780
cacatttcca cagaccgtaa tttcatgtct cactttctct tttgctcttc ttttacttag 840
tcaggtttga taacttcctt ttttattacc ctatcttatt tatttattta ttcatttata 900
ccaaccaacc 910

<210> SEQ ID NO 35
<211> LENGTH: 908
<212> TYPE: DNA
<213> ORGANISM: Artificial Sequence
<220> FEATURE:
<223> OTHER INFORMATION: 346delT, 352C>A, 354delG, 598A>G, 765_766AC>TT,
774insTT and 1170_1173delACCA

<400> SEQUENCE: 35
gtcgacttct cctttaggca atagaaaaag actaagagaa cagcgttttt acaggttgca 60
ttggttaatg tagtattttt tagtccaaca ttctgtgggt tgctctgggt ttctagaata 120
ggaaatcaca ggagaatgca aattcagatg gaagaacaaa gagataaaaa acaaaaaaaa 180
actgagtttt gcaccaatag aatgtttgat gatatcatcc actcgctaaa cgaatcatgt 240
gggtgatctt ctctttagtt ttggtctatc ataaaacaca tgaaagtgaa atccaaatac 300
actacactcc gggtattgtc cttcgtttta cggatgtctc attgtcttac ttttgaggtc 360
ataggagttg cctgtgagag atcacagaga ttatcacact cacatttatc gtagtttcct 420
atctcatgct gtgtgtctct ggttggttca tgagtttgga ttgttgtaca ttaaaggaat 480
cgctggaaag caaagctatt taaatttttt ctttgtcaca ggtacactaa cctgtaaaac 540
ttcactgcca cgccagtctt tcctgattgg gcaagtgcac aaactacaac ctgcaaaaca 600
gcactccgct tgtcacaggt tgtctcctct caaccaacaa aaaaataaga ttaaactttc 660
tttgctcatg catcaatcgg agttatctct gaaagagttg cctttgtgta atgtgtgcca 720
aactcaaact gcaaaactaa ccacagaatg atttccctca caattatata aactcaccca 780
catttccaca gaccgtaatt tcatgtctca ctttctcttt tgctcttctt ttacttagtc 840
aggtttgata acttcctttt ttattaccct atcttattta tttatttatt catttatacc 900
aaccaacc 908

<210> SEQ ID NO 36
<211> LENGTH: 908
<212> TYPE: DNA
<213> ORGANISM: Artificial Sequence
<220> FEATURE:
<223> OTHER INFORMATION: 301A>G, 324A>T, 346delT, 352C>A, 354delG,
598A>G, 765_766AC>TT, 774insTT, and 1170_1173delACCA

<400> SEQUENCE: 36

```
gtcgacttct cctttaggca atagaaaaag actaagggaa cagcgttttt acaggttgct     60

ttggttaatg tagtattttt tagtccaaca ttctgtgggt tgctctgggt ttctagaata    120

ggaaatcaca ggagaatgca aattcagatg gaagaacaaa gagataaaaa acaaaaaaaa    180

actgagtttt gcaccaatag aatgtttgat gatatcatcc actcgctaaa cgaatcatgt    240

gggtgatctt ctctttagtt ttggtctatc ataaaacaca tgaaagtgaa atccaaatac    300

actacactcc gggtattgtc cttcgtttta cggatgtctc attgtcttac ttttgaggtc    360

ataggagttg cctgtgagag atcacagaga ttatcacact cacatttatc gtagtttcct    420

atctcatgct gtgtgtctct ggttggttca tgagtttgga ttgttgtaca ttaaaggaat    480

cgctggaaag caaagctatt taaatttttt ctttgtcaca ggtacactaa cctgtaaaac    540

ttcactgcca cgccagtctt tcctgattgg gcaagtgcac aaactacaac ctgcaaaaca    600

gcactccgct tgtcacaggt tgtctcctct caaccaacaa aaaaataaga ttaaactttc    660

tttgctcatg catcaatcgg agttatctct gaaagagttg cctttgtgta atgtgtgcca    720

aactcaaact gcaaaactaa ccacagaatg atttccctca caattatata aactcaccca    780

catttccaca gaccgtaatt tcatgtctca ctttctcttt tgctcttctt ttacttagtc    840

aggtttgata acttcctttt ttattaccct atcttattta tttatttatt catttatacc    900

aaccaacc                                                              908
```

<210> SEQ ID NO 37
<211> LENGTH: 16
<212> TYPE: DNA
<213> ORGANISM: Candida tropicalis

<400> SEQUENCE: 37

```
accaaccaac caacca                                                      16
```

<210> SEQ ID NO 38
<211> LENGTH: 12
<212> TYPE: DNA
<213> ORGANISM: Artificial Sequence
<220> FEATURE:
<223> OTHER INFORMATION: part of mutated promoter sequence

<400> SEQUENCE: 38

```
accaaccaac ca                                                          12
```

<210> SEQ ID NO 39
<211> LENGTH: 15
<212> TYPE: DNA
<213> ORGANISM: Artificial Sequence
<220> FEATURE:
<223> OTHER INFORMATION: 765-766AC>TT, 774insTT

<400> SEQUENCE: 39

```
accaaccaac caacc                                                       15
```

-continued

```
<210> SEQ ID NO 40
<211> LENGTH: 11
<212> TYPE: DNA
<213> ORGANISM: Artificial Sequence
<220> FEATURE:
<223> OTHER INFORMATION: 1170-1173delACCA

<400> SEQUENCE: 40

accaaccaac c                                                            11
```